US012264350B2

(12) United States Patent
Fukunaga et al.

(10) Patent No.: US 12,264,350 B2
(45) Date of Patent: Apr. 1, 2025

(54) METHOD FOR PRODUCING SULFATED POLYSACCHARIDE AND METHOD FOR PRODUCING PAPS

(71) Applicants: RENSSELAER POLYTECHNIC INSTITUTE, Troy, NY (US); OTSUKA PHARMACEUTICAL FACTORY, INC., Naruto (JP); KIRIN BIOMATERIALS CO., LTD., Tokyo (JP)

(72) Inventors: Kenta Fukunaga, Tokyo (JP); Aki Nishibara, Tokyo (JP); Ryosuke Kato, Tokyo (JP); Masahiro Kuratsu, Tokyo (JP); Mikiro Hayashi, Tokyo (JP); Shin-ichi Hashimoto, Tokyo (JP)

(73) Assignees: RENSSELAER POLYTECHNIC INSTITUTE, Troy, NY (US); OTSUKA PHARMACEUTICAL FACTORY, INC., Naruto (JP); KIRIN BIOMATERIALS CO., LTD., Tokyo (JP)

( * ) Notice: Subject to any disclaimer, the term of this patent is extended or adjusted under 35 U.S.C. 154(b) by 44 days.

(21) Appl. No.: 17/995,367

(22) PCT Filed: Apr. 2, 2021

(86) PCT No.: PCT/JP2021/014337
§ 371 (c)(1),
(2) Date: Oct. 3, 2022

(87) PCT Pub. No.: WO2021/201282
PCT Pub. Date: Oct. 7, 2021

(65) Prior Publication Data
US 2023/0159969 A1 May 25, 2023

(30) Foreign Application Priority Data

Apr. 3, 2020 (WO) .................. PCT/JP2020/015388

(51) Int. Cl.
*C12P 19/04* (2006.01)
*C12N 9/12* (2006.01)
*C12P 19/26* (2006.01)

(52) U.S. Cl.
CPC ............ *C12P 19/26* (2013.01); *C12N 9/1205* (2013.01); *C12N 9/1241* (2013.01); *C12P 19/04* (2013.01); *C12Y 207/01025* (2013.01); *C12Y 207/07004* (2013.01)

(58) Field of Classification Search
CPC ........... C12P 19/26; C12P 19/04; C12P 19/32; C12N 9/1205; C12N 9/1241; C12N 15/77; C12Y 207/01025; C12Y 207/07004
See application file for complete search history.

(56) References Cited

U.S. PATENT DOCUMENTS

| | | | |
|---|---|---|---|
| 5,376,535 A | 12/1994 | Onda et al. | |
| 8,771,995 B2 | 7/2014 | Liu et al. | |
| 2002/0001831 A1 | 1/2002 | Defrees et al. | |
| 2009/0215114 A1 | 8/2009 | Ishige et al. | |
| 2012/0157669 A1 | 6/2012 | Wang et al. | |
| 2012/0244580 A1 | 9/2012 | Hung et al. | |
| 2012/0322114 A1 | 12/2012 | Liu et al. | |
| 2014/0199732 A1 | 7/2014 | Kim et al. | |
| 2017/0204443 A1 | 7/2017 | Baumgärtner et al. | |
| 2019/0284590 A1 | 9/2019 | Jendresen et al. | |

FOREIGN PATENT DOCUMENTS

| | | |
|---|---|---|
| EP | 1842910 A1 | 10/2007 |
| JP | H05-137588 A | 6/1993 |
| JP | 2002-530087 A | 9/2002 |
| JP | 4505011 B2 | 7/2010 |
| JP | 2012-201665 A | 10/2012 |
| JP | 2013-501519 A | 1/2013 |
| JP | 2014-525244 A | 9/2014 |
| JP | 5830464 B2 | 12/2015 |

(Continued)

OTHER PUBLICATIONS

Russian Federal Service for Intellectual Property, Official Action and Search Report in Russian Patent Application No. 2022125495(055557) (Apr. 17, 2023).
Joo et al., "Metabolic Design of *Corynebacterium glutamicum* for Production of $_L$-Cysteine with Consideration of Sulfur-Supplemented Animal Feed," *J. Agric. Food. Chem.*, 65(23): 4698-4707 (2017).
IP Australia, Examination Report in Australian Patent Application No. 2021249958 (Sep. 15, 2023).
Japan Patent Office, Notification of Reasons for Refusal in Japanese Patent Application No. 2022-560338 (Jul. 11, 2023).

(Continued)

*Primary Examiner* — Satyendra K Singh
(74) *Attorney, Agent, or Firm* — Leydig, Voit & Mayer, Ltd.

(57) ABSTRACT

The invention provides a method for producing sulfated polysaccharides by reacting a PAPS production/regeneration system utilizing the metabolic activity of a microorganism or a treated matter thereof with a microorganism expressing a sulfation enzyme or a treated matter or extract thereof upon mixing of inexpensive raw materials such as magnesium sulfate. The invention also provides a method for producing PAPS from inexpensive raw materials. The methods involve preparing a transformant (a) of a bacterium of the genus *Corynebacterium*, which contains a gene encoding an ATP sulfurylase and a gene encoding an APS kinase, which are expressible, and in which a cell plasma membrane of the transformant (a) is substance-permeable, or a treated matter of the transformant (a), and conducting a reaction for producing PAPS by using a reaction solution containing ATP or an ATP source, a sulfate ion source, and the transformant (a) or the treated matter thereof.

10 Claims, 5 Drawing Sheets
Specification includes a Sequence Listing.

(56) References Cited

FOREIGN PATENT DOCUMENTS

| JP | 2017-520267 A | 7/2017 | |
|---|---|---|---|
| JP | WO 2019050051 A1 * | 3/2019 | ............. C12N 15/70 |
| WO | WO 1996/029424 A1 | 9/1996 | |
| WO | WO 2000/029603 A2 | 5/2000 | |
| WO | WO 2000/029603 A3 | 5/2000 | |
| WO | WO 2006/124801 A2 | 11/2006 | |
| WO | WO 2012/057336 A1 | 5/2012 | |
| WO | WO 2016/008602 A1 | 1/2016 | |
| WO | WO 2018/048973 A1 | 3/2018 | |
| WO | WO 2020/013346 A1 | 1/2020 | |

OTHER PUBLICATIONS

Japan Patent Office, Decision to Grant a Patent in Japanese Patent Application No. 2022-560338 (Oct. 31, 2023).
Japan Patent Office, Notification of Reasons for Refusal in Japanese Patent Application No. 2022-560338 (Feb. 21, 2023).
Bhaskar et al., "Combinatorial One-pot Chemoenzymatic Synthesis of Heparin," *Carbohydrate Polymers*, 122: 399-407 (2015).
Fu et al., "Bioengineered Heparins and Heparan Sulfates," *Adv. Drug. Deliv. Rev.*, 97: 237-249 (2016).
He et al., "Production of Chondroitin in Metabolically Engineered *E. coli*," *Metab. Eng.*, 27: 92-100 (2015).
Maruyama et al., "ATP Production from Adenine by a Self-coupling Enzymatic Process: High-level Accumulation under Ammonium-limited Conditions," *Biosci. Biotechnol. Biochem.*, 65(3): 644-650 (2001).
Zhou et al., "A Microbial-enzymatic Strategy for Producing Chondroitin Sulfate Glycosaminoglycans," *Biotechnol. Bioeng.*, 115(6): 1561-1570 (2018).
Zhou et al., "Expression of Heparan Sulfate Sulfotransferases in *Kluyveromyces lactis* and Preparation of 3'-Phosphoadenosine-5'-Phosphosulfate," *Glycobiology.*, 21(6): 771-780 (2011).
Japan Patent Office, International Search Report in International Patent Application No. PCT/JP2020/015388 (Jul. 7, 2020).
Japan Patent Office, Written Opinion of the International Searching Authority in International Patent Application No. PCT/JP2020/015388 (Jul. 7, 2020).
Japan Patent Office, International Search Report in International Patent Application No. PCT/JP2021/014337 (Jun. 22, 2021).
Japan Patent Office, Written Opinion of the International Searching Authority in International Patent Application No. PCT/JP2021/014337 (Jun. 22, 2021).
Saudi Authority for Intellectual Property, Substantive Examination Report in Saudi Arabian Patent Application No. 522440743 (May 31, 2023).
Genbank, "3'-Phosphoadenosine 5'-phosphosulfate (PAPS) 3'-phosphatase [Corynebacterium glutamicum ATCC 13032]" GenBank Database Accession No. CAF19551 (Feb. 27, 2015) [accessed from: https://ncbi.nlm.nih.gov/protein/CAF19551].
Canadian Intellectual Property Office, Office Action in Canadian Patent Application No. 3, 174,029 (Mar. 6, 2024).
Intellectual Property Office of Singapore, Written Opinion in Singaporean Patent Application No. 11202253757C (Mar. 8, 2024).
IP Australia, Examination Report in Australian Patent Application No. 2021249958 (Feb. 28, 2024).
Saudi Authority for Intellectual Property, Substantive Examination Report in Saudi Arabian Patent Application No. 522440743 (Nov. 27, 2023).
Donalies et al., "Increasing Sulphite Formation in *Saccharomyces cerevisiae* by Overexpression of METI4 and SSUI," *Yeast*, 19(6): 475-484 (2002).
Rückert et al., "Functional Genomics and Expression Analysis of the *Corynebacterium glutamicum* fpr2-cysIXHDNYZ Gene Cluster Involved in Assimilatory Sulphate Reduction," *BMC Genomics*, 6: 121 (2005).
European Patent Office, Extended European Search Report in European Patent Application No. 21780255.2 (May 29, 2024).
Korean Intellectual Property Office, Office Action in Korean Patent Application No. 10-2022-7034289 (Oct. 21, 2024).
Taiwan Intellectual Property Office, Office Action in Taiwanese Patent Application No. 110112230 (Aug. 16, 2024).

\* cited by examiner

[Fig. 1]
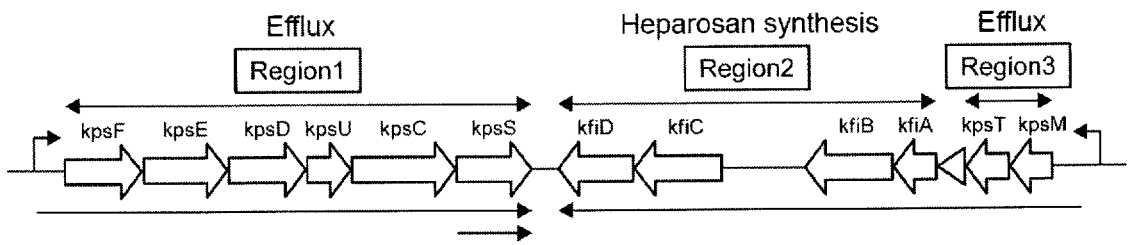
[Fig. 2]
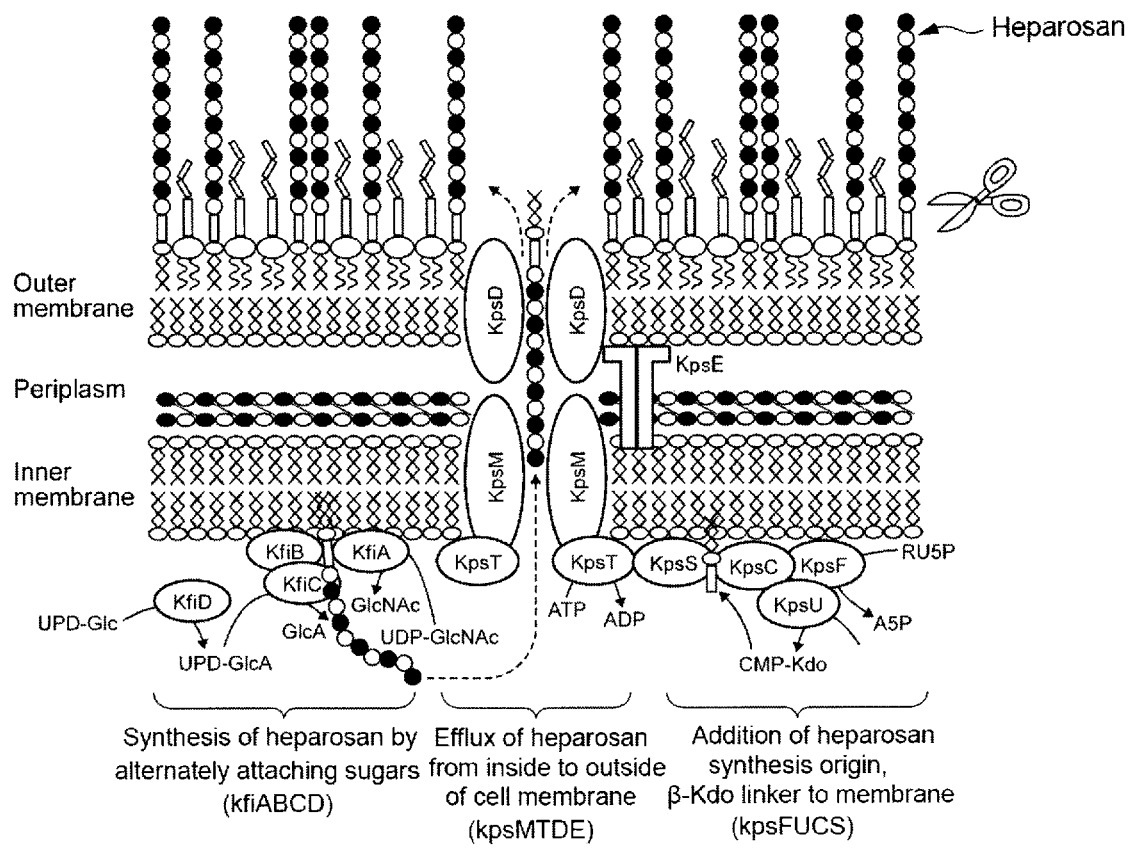

[Fig. 3]
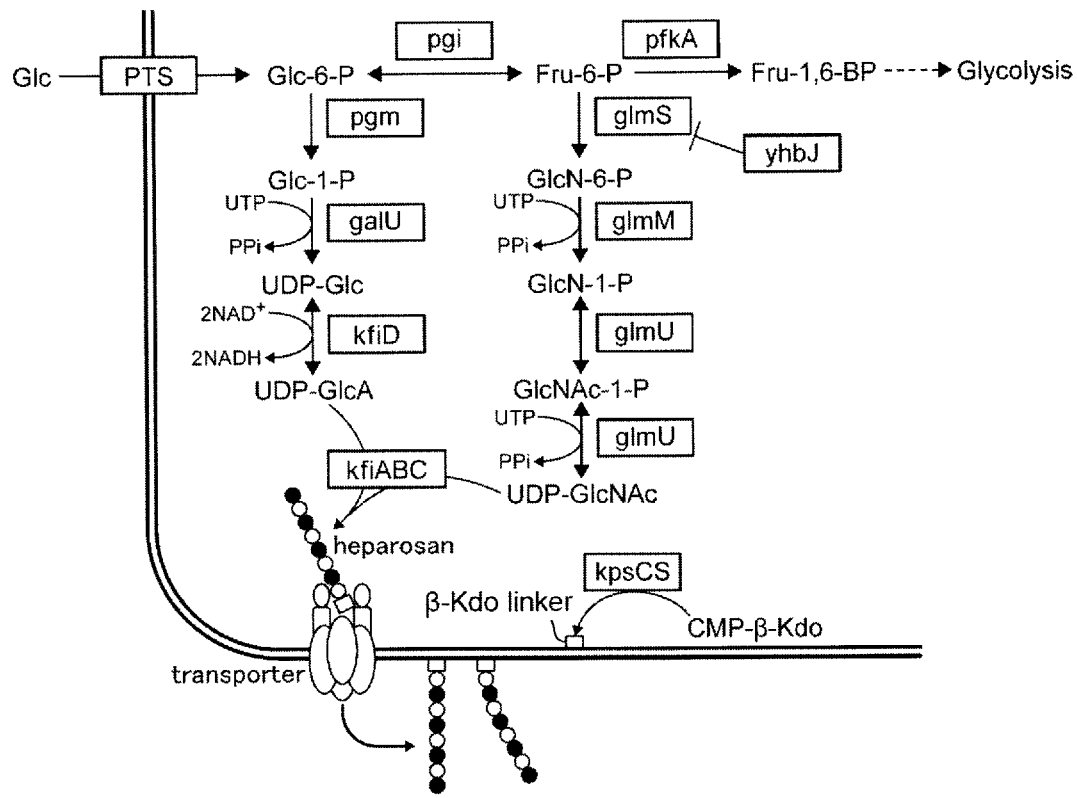
[Fig. 4]
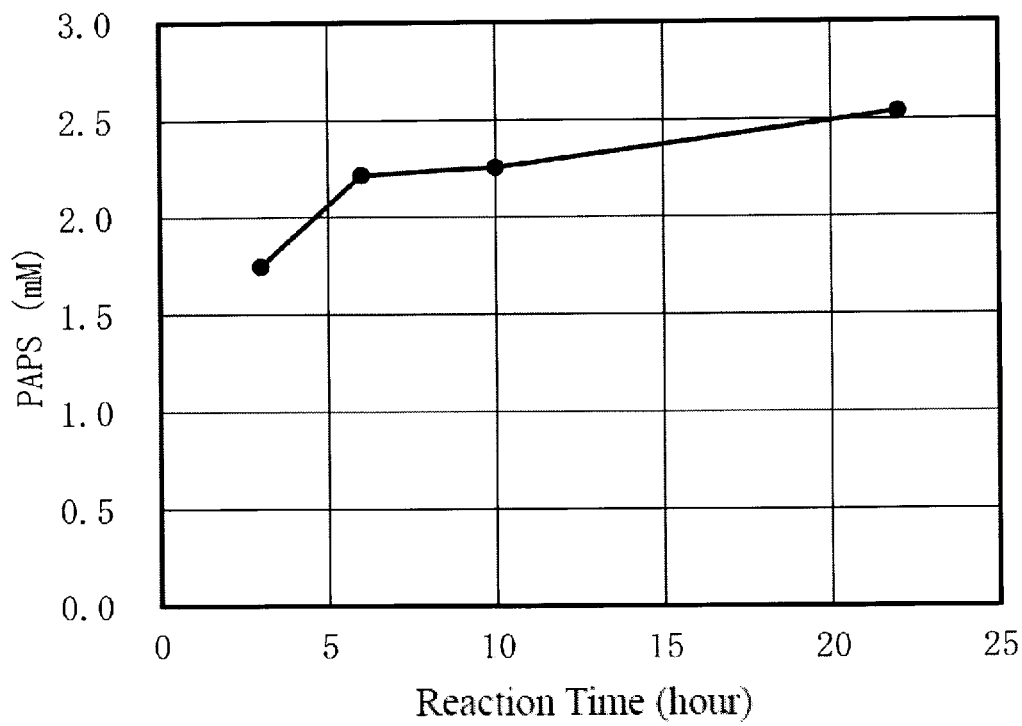

[Fig. 5]
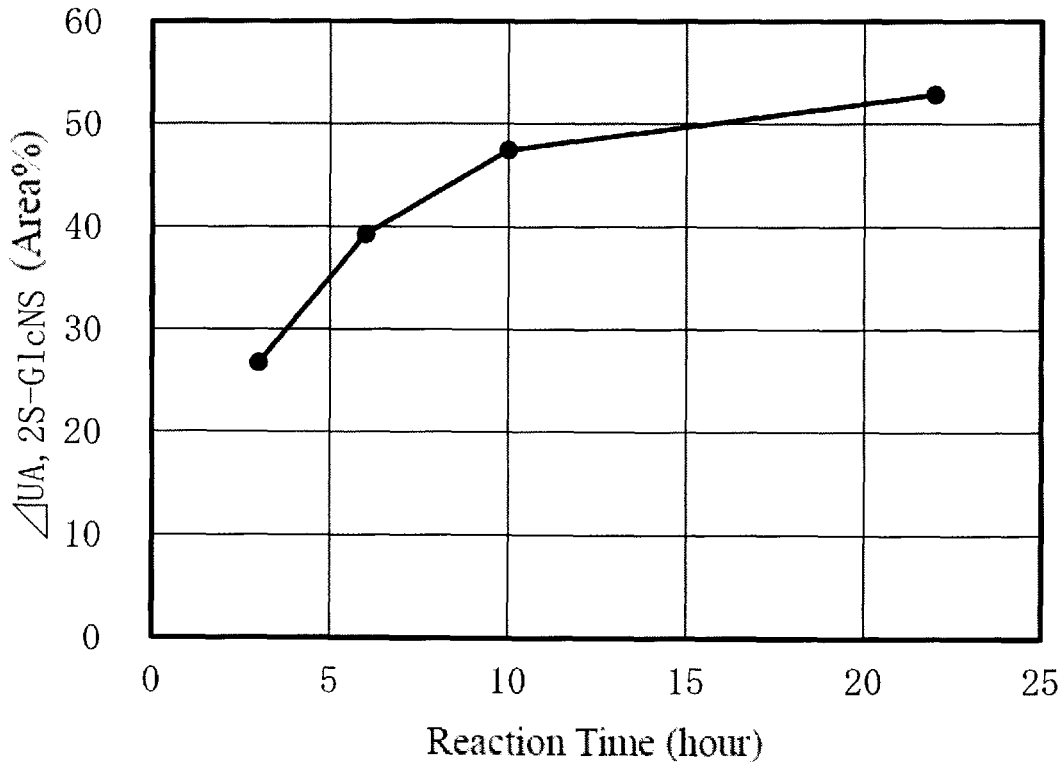
[Fig. 6]
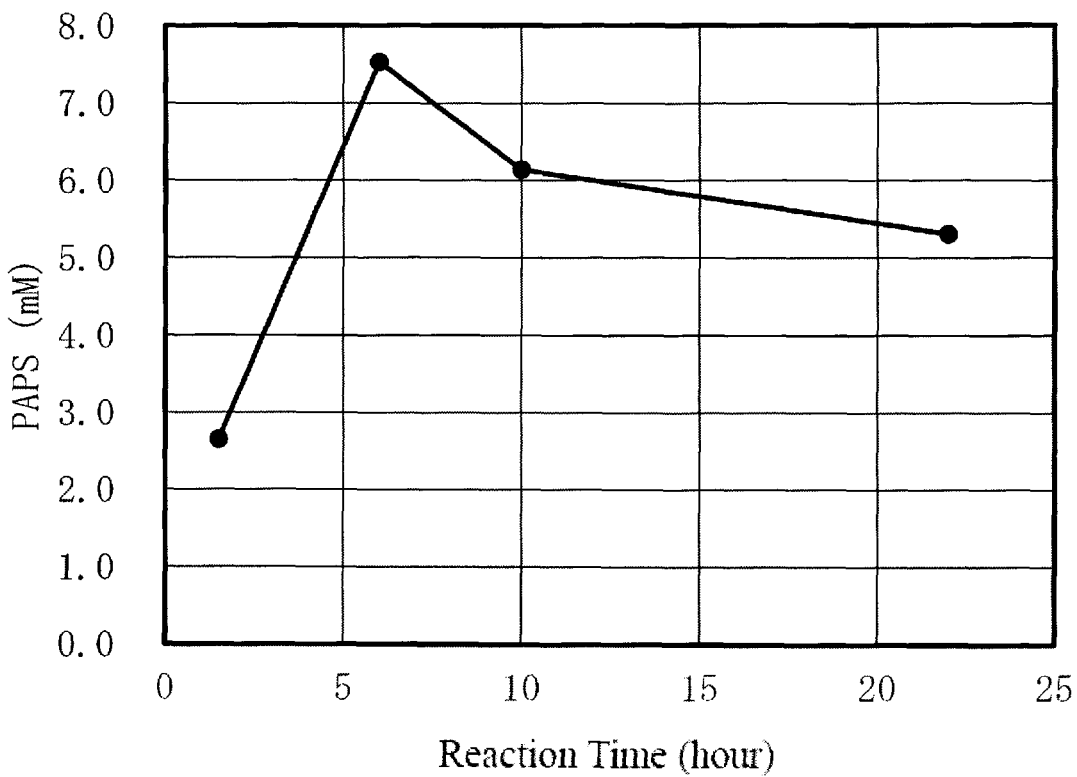

[Fig. 7]
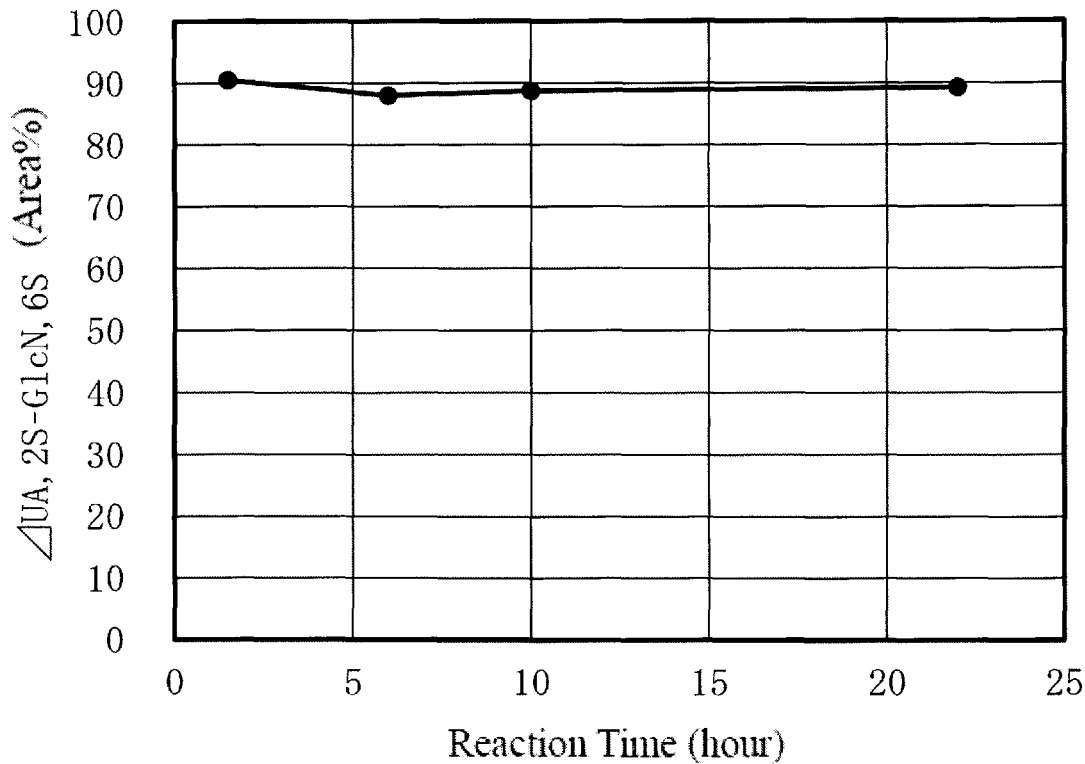
[Fig. 8]
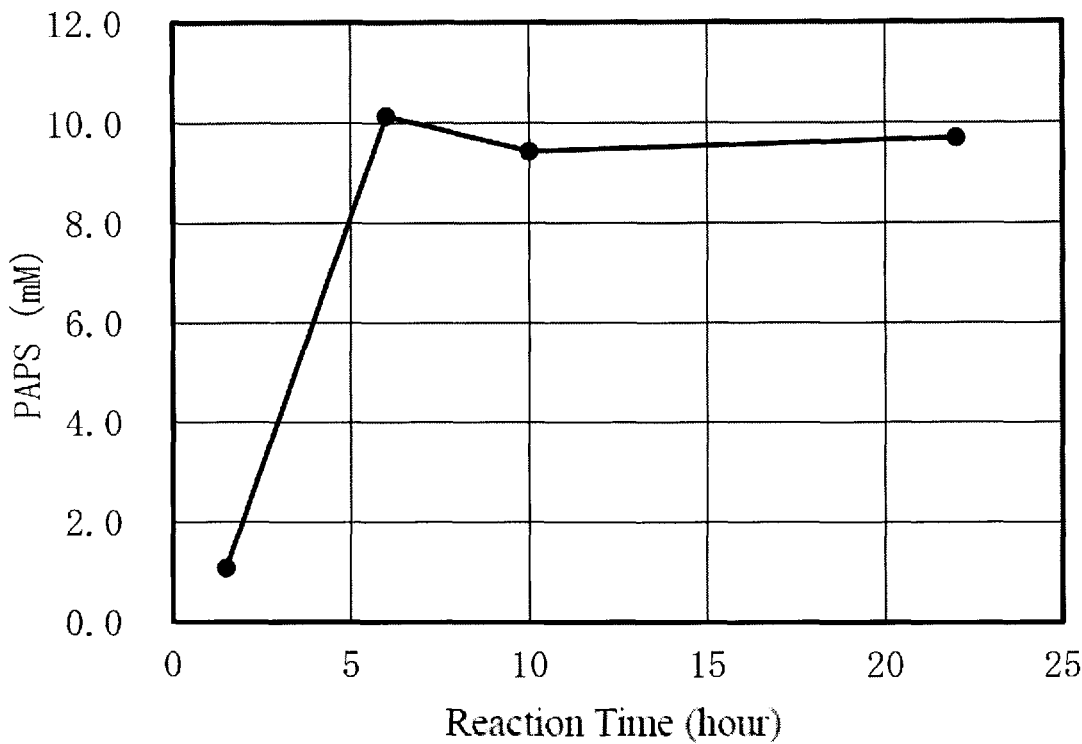

[Fig. 9]
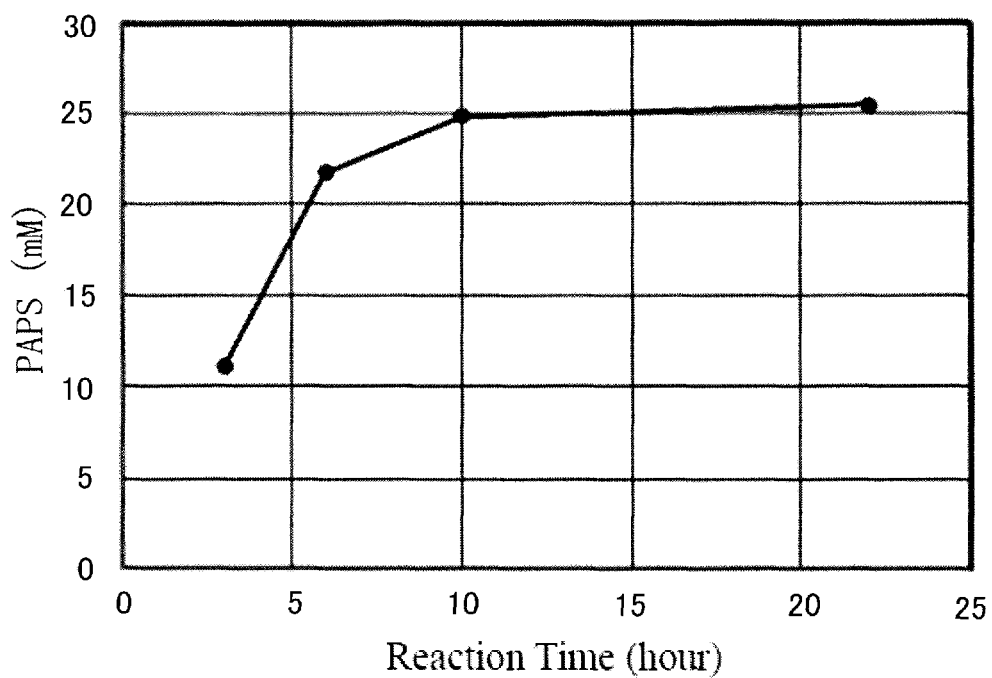

METHOD FOR PRODUCING SULFATED POLYSACCHARIDE AND METHOD FOR PRODUCING PAPS

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 25,035 Byte ASCII (Text) file named "764676_ST25.txt," created on Sep. 19, 2022.

TECHNICAL FIELD

The present invention relates to a method for producing 3'-phosphoadenosine 5'-phosphosulfate (hereinafter referred to as PAPS) from inexpensive raw materials such as glucose and adenine using a bacteria of the genus *Corynebacterium* expressing an ATP sulfurylase and an APS kinase (an adenylylsulfate kinase), and a method for producing a sulfated polysaccharide using the bacterium of the genus *Corynebacterium* and a microorganism belonging to prokaryotes expressing various sulfation enzymes.

BACKGROUND ART

PAPS is a coenzyme that exists widely from microorganisms to higher organisms and functions as a donor of a sulfate group in vivo. In higher organisms, PAPS is required for biosynthesis of glycosaminoglycans such as chondroitin sulfate and heparan sulfate. It is known that sulfated in vivo metabolites have various physiological functions, and PAPS itself is expected to be used as a hair restorer (PTL 1), an external preparation for skin having moisturizing effect (PTL 2), and the like.

As a method for producing PAPS, a method of using an ATP sulfurylase derived from purified yeast, an APS kinase derived from blue mold, and a pyrophosphatase derived from *Escherichia coli*, with use of ATP as a raw material (NPL 1); a method of using a thermostable ATP sulfurylase derived from a thermophilic bacterium, an APS kinase, and a pyrophosphatase derived from yeast, with use of ATP as a raw material as in the above method (PTL 3); a method of using an ATP sulfurylase derived from a thermostable bacterium, an APS kinase, and a polyphosphate kinase derived from *Pseudomonas aeruginosa*, with use of adenosine 5'-monophosphate (hereinafter referred to as AMP) as a raw material (PTL 4); and the like are known.

Meanwhile, a method for industrially producing ATP by using a mutant strain of *Corynebacterium ammoniagenes*, in which the membrane of the bacterial cells is treated with xylene or a surfactant to impart permeability thereto, with use of inexpensive raw materials such as glucose and adenine is known (NPL 2).

PAPS is a very unstable compound. Even in a method using a crude enzyme, PAPS is produced by preparing a crude enzyme of an APS kinase and an ATP sulfurylase derived from a thermostable bacterium which is recombinantly expressed by *Escherichia coli* as a host, followed by heating treatment before a reaction, thereby suppressing an activity of contaminating enzymes derived from *Escherichia coli* (PTL 4).

PTL8 discloses that PAPS is degraded in a crude enzyme solution of *Escherichia coli*. *Escherichia coli* has some enzymes relating to degradation of PAPS and it is possible to inhibit the degradation of PAPS by deleting a gene of such enzymes.

Heparin, which is a sulfated polysaccharide, is a major anticoagulant agent, and is used for thromboembolism and disseminated intravascular coagulation syndrome, and for prevention of coagulation during artificial dialysis and in extracorporeal circulation, and the like. Industrially, most heparin is extracted and purified from the intestinal mucosa of pigs. Since a fatal accident occurred in 2008 due to contamination of pig-derived heparin with impurities, research and development of non-animal sourced production-controlled/quality-controlled heparin have been conducted.

As a specific example, a method in which fermentatively produced and purified N-acetylheparosan (hereinafter referred to as heparosan), which is a capsular polysaccharide of some Gram-negative microorganisms, is chemically N-deacetylated and N-sulfated, followed by enzymatic epimerization and sulfation to yield heparin having the same structure and anticoagulation activity as those derived from pigs (PTLs 5 to 7, and NPLs 3 and 4).

Chondroitin sulfate is known as another useful sulfated polysaccharide, and it has been used as a drug for joint pain and eye drops for protecting the corneal surface layer. Chondroitin sulfate extracted and purified from various animal tissues has been used, but a method using a sulfation enzyme, with use of a capsular polysaccharide derived from *Escherichia coli* as a raw material, in the same manner as heparin has been reported recently (NPLs 5 and 6).

In a method of performing sulfation using a purified enzyme, with use of a polysaccharide derived from a capsule of a microorganism as a raw material, PAPS serves as a donor of a sulfate group in the reaction of a sulfation enzyme and is required as a coenzyme. In the above-mentioned method for producing a sulfated polysaccharide using a capsular polysaccharide derived from the capsule of a microorganism as a raw material, 3'-phosphoadenosine 5'-phosphate (hereinafter, referred to as PAP) is generated by a sulfate group transfer of PAPS to the substrate polysaccharide, a sulfate group of p-nitrophenyl sulfate is enzymatically transferred to the PAP, thereby regenerating PAPS, and an enzymatic sulfation reaction of the polysaccharide is advanced (PTL 6 and NPL 3).

CITATION LIST

Patent Literature

PTL 1: WO2012/057336
PTL 2: JP-A-2012-201665
PTL 3: JP-A-H5-137588
PTL 4: Japanese Patent No. 4505011
PTL 5: Japanese Patent No. 5830464
PTL 6: U.S. Pat. No. 8,771,995
PTL 7: WO2018/048973
PTL 8: WO2020/013346

Non Patent Literature

NPL 1: Glycobiology vol. 21, no. 6, pp. 771-780, 2011
NPL 2: Biosci. Biotechnol. Biochem. 65 (3), 644-650, 2001
NPL 3: Carbohydrate Polymers 122 (2015) 399-407
NPL 4: Advanced Drug Delivery Reviews 97 (2016) 237-249
NPL 5: Metabolic Engineering 27 (2015) 92-100

NPL 6: Biotechnology and Bioengineering 115 (2018) 1561-1570

SUMMARY OF INVENTION

Technical Problem

The conventional methods for producing PAPS described in NPL 1 and PTLs 1 and 2 each use relatively expensive nucleotides such as ATP and AMP as raw materials, and use an enzyme or a crude enzyme which is prepared by culturing bacteria, followed by separation of the bacterial cells, disruption of the bacterial cells by sonication or the like, and centrifugation. Therefore, it is not easy to carry out those methods on an industrial scale.

On the other hand, as described above, for the production of PAPS, a method using a purified enzyme or a crude enzyme, with use of ATP or AMP as a raw material is known, but an example of producing PAPS using a microorganism itself is not known. In addition, as described above, PAPS is a very unstable compound, and in the prior art, in a case where a crude enzyme is used, complicated steps such as suppressing the activity of contaminating enzymes by heat treatment are performed.

In view of the above, it is difficult to predict that PAPS can be produced by a method similar to that for industrially producing ATP simply by expressing ATP sulfurylase and APS kinase in a bacterium of the genus *Corynebacterium* as a host. This is because, as in the case of *Escherichia coli*, the genus *Corynebacterium* also has some enzymes relating to the degradation of PAPS.

In addition, as described above, the conventional method for enzymatically sulfating polysaccharides uses a plurality of sulfation enzymes purified from a cell lysate which is prepared by culturing microorganisms expressing a sulfation enzyme, followed by collection, and sonication or the like. These methods were not easy to implement on an industrial scale. In addition, expensive PAPS and p-nitrophenyl sulfate were required as raw materials.

Accordingly, an object of the present invention is to provide a method for easily producing sulfated polysaccharides by reacting a PAPS production/regeneration system utilizing the metabolic activity of a microorganism or a treated matter thereof with a microorganism expressing a sulfation enzyme or a treated matter or extract thereof upon mixing of inexpensive raw materials such as magnesium sulfate. Another object of the present invention is to provide a practical method for producing PAPS from inexpensive raw materials.

Solution to Problem

The inventors of the present invention have completed the present invention based on the following findings (1) and (2).

(1) PAPS can be produced more easily and inexpensively, as compared to methods of the related art, by culturing a strain in which ATP sulfurylase and APS kinase activities are enhanced by recombinant DNA techniques using a bacterium of the genus *Corynebacterium* having an ATP-producing ability as a host, imparting membrane permeability thereto with surfactants or the like, and adding raw materials such as glucose and adenine.

(2) Sulfated polysaccharides can be produced using bacterial cells and inexpensive raw materials such as magnesium sulfate, without enzyme purification or PAPS addition, by using the strain with enhanced ATP sulfurylase and APS kinase activities described in (1) as a microbial bacterial cell responsible for PAPS production/regeneration reaction, imparting membrane permeability to a microorganism belonging to prokaryotes that express an epimerase and/or sulfation enzymes, and performing a mixed reaction.

That is, the present invention is as follows.

1. A method for producing a sulfated polysaccharide, the method comprising the following steps (1-1) and (1-2):
   (1-1) preparing a transformant (a) of a bacterium of the genus *Corynebacterium*, comprising at least a gene encoding an ATP sulfurylase and a gene encoding an APS kinase which are introduced thereinto in an expressible manner, or a treated matter of the transformant (a); and
   (1-2) conducting a reaction for producing PAPS by using a reaction solution containing ATP or an ATP source, a sulfate ion source, and the transformant (a) or the treated matter thereof.

2. The method for producing a sulfated polysaccharide according to 1, the method further comprising the following steps (2-1) and (2-2):
   (2-1) preparing a transformant (b) of a microorganism belonging to prokaryotes, comprising at least a gene encoding a C5-epimerase which is introduced thereinto in an expressible manner, or a treated matter or extract of the transformant (b); and
   (2-2) conducting C5-epimerization by incorporating the transformant (b) or the treated matter or extract thereof in the reaction solution in the presence of N-sulfoheparosan.

3. The method for producing a sulfated polysaccharide according to 1 or 2, comprising conducting sulfation by a transformant comprising a gene encoding sulfotransferase, which is introduced thereinto in an expressible manner, or a treated matter or extract of the transformant.

4. The method for producing a sulfated polysaccharide according to 3, the method further comprising the following steps (3-1) and (3-2):
   (3-1) preparing a transformant (c) of a microorganism belonging to prokaryotes, comprising at least a gene encoding a 2-O-sulfotransferase which is introduced thereinto in an expressible manner, or a treated matter or extract of the transformant (c); and
   (3-2) conducting 2-O-sulfation by incorporating the transformant (c) or the treated matter or extract thereof in the reaction solution in the presence of N-sulfoheparosan.

5. The method for producing a sulfated polysaccharide according to 3 or 4, the method further comprising the following steps (3'-1) to (3'-3):
   (3'-1) preparing a transformant (b) of a microorganism belonging to prokaryotes, comprising at least a gene encoding a C5-epimerase which is introduced thereinto in an expressible manner, or a treated matter or extract of the transformant (b);
   (3'-2) preparing a transformant (c) of a microorganism belonging to prokaryotes, comprising at least a gene encoding a 2-O-sulfotransferase which is introduced thereinto in an expressible manner, or a treated matter or extract of the transformant (c); and
   (3'-3) conducting C5-epimerization and 2-O-sulfation by incorporating the transformant (b) or the treated matter or extract thereof, and the transformant (c) or the treated matter or extract thereof in the reaction solution in the presence of N-sulfoheparosan.

6. The method for producing a sulfated polysaccharide according to any one of 3 to 5, the method further comprising the following steps (4-1) and (4-2):

(4-1) preparing a transformant (d) of a microorganism belonging to prokaryotes, comprising at least a gene encoding a 6-O-sulfotransferase which is introduced thereinto in an expressible manner, or a treated matter or extract of the transformant (d); and (4-2) conducting 6-O-sulfation by incorporating the transformant (d) or the treated matter or extract thereof in the reaction solution in the presence of N-sulfoheparosan.

7. The method for producing a sulfated polysaccharide according to any one of 3 to 6, the method further comprising the following steps (5-1) and (5-2):

(5-1) preparing a transformant (e) of a microorganism belonging to prokaryotes, comprising at least a gene encoding a 3-O-sulfotransferase which is introduced thereinto in an expressible manner, or a treated matter or extract of the transformant (e); and (5-2) conducting 3-O-sulfation by incorporating the transformant (e) or the treated matter or extract thereof in the reaction solution in the presence of N-sulfoheparosan.

8. A method for producing a sulfated polysaccharide, the method comprising generating a sulfated polysaccharide by incorporating, in a reaction solution in the presence of ATP or an ATP source, a sulfate ion source, and N-sulfoheparosan, a transformant (a) of a bacterium of the genus *Corynebacterium*, comprising at least a gene encoding an ATP sulfurylase and a gene encoding an APS kinase which are introduced thereinto in an expressible manner, or a treated matter of the transformant (a), and at least one selected from:

a transformant (b) of a microorganism belonging to prokaryotes, comprising at least a gene encoding a C5-epimerase which is introduced thereinto in an expressible manner, or a treated matter or extract of the transformant (b), a transformant (c) of a microorganism belonging to prokaryotes, comprising at least a gene encoding a 2-O-sulfotransferase which is introduced thereinto in an expressible manner, or a treated matter or extract of the transformant (c), a transformant (d) of a microorganism belonging to prokaryotes, comprising at least a gene encoding a 6-O-sulfotransferase which is introduced thereinto in an expressible manner, or a treated matter or extract of the transformant (d), and a transformant (e) of a microorganism belonging to prokaryotes, comprising at least a gene encoding a 3-O-sulfotransferase which is introduced thereinto in an expressible manner, or a treated matter or extract of the transformant (e).

9. The method for producing a sulfated polysaccharide according to 7, the method further comprising generating a sulfated polysaccharide by incorporating, in the reaction solution in the presence of ATP or the ATP source, the sulfate ion source, and N-sulfoheparosan, the transformant (a) or the treated matter thereof, and the transformants (b) to (e) or the treated matters or extracts thereof.

10. The method for producing a sulfated polysaccharide according to any one of 1 to 9, which is for producing heparin.

11. A method for producing PAPS, the method comprising the following steps (i) and (ii):

(i) preparing a transformant of a bacterium of the genus *Corynebacterium*, comprising at least a gene encoding an ATP sulfurylase and a gene encoding an APS kinase which are introduced thereinto in an expressible manner, or a treated matter of the transformant; and (ii) conducting a reaction for producing PAPS by using a reaction solution containing ATP or an ATP source, a sulfate ion source, and the transformant prepared in the step (i) or the treated matter thereof.

Advantageous Effects of Invention

According to the method for producing a sulfated polysaccharide of the present invention, sulfated polysaccharides can be produced easily and inexpensively by using a PAPS production/regeneration system utilizing the metabolic activity of a microorganism, and a microorganism expressing a sulfation enzyme or a treated matter or extract thereof. In addition, according to the method for producing PAPS of the present invention, PAPS can be produced easily and inexpensively by utilizing the metabolic activity of a microorganism or a treated matter thereof. Furthermore, by using the genus *Corynebacterium* in the method of the present invention, it is not necessary to modify genes in a complex manner for avoiding degradation of PAPS.

BRIEF DESCRIPTION OF DRAWINGS

FIG. 1 shows a schematic diagram of a heparosan synthesis gene cluster on the chromosome of an *Escherichia coli* K5 strain.

FIG. 2 shows a schematic diagram of an enzyme involved in heparosan production.

FIG. 3 shows a schematic diagram of a heparosan biosynthetic pathway.

FIG. 4 is a graph showing time-dependent changes in concentration of PAPS contained in a supernatant of a reaction solution in a 2-O-sulfation reaction test of N-sulfoheparosan.

FIG. 5 is a graph showing time-dependent changes in area ratio of delta-UA, 2S-GlcNS in unsaturated disaccharide HPLC analysis in the 2-O-sulfation reaction test of N-sulfoheparosan.

FIG. 6 is a graph showing time-dependent changes in concentration of PAPS contained in a supernatant of a reaction solution in a 6-O-sulfation reaction test of 2-O-sulfated N-sulfoheparosan.

FIG. 7 is a graph showing time-dependent changes in area ratio of delta-UA, 2S-GlcN, 6S in unsaturated disaccharide HPLC analysis in the 6-O-sulfation reaction test of 2-O-sulfated N-sulfoheparosan.

FIG. 8 is a graph showing time-dependent changes in concentration of PAPS contained in a supernatant of a reaction solution in a 6-O-position and 3-O-position sulfation reaction test of 2-O-sulfated N-sulfoheparosan.

FIG. 9 is a graph showing time-dependent changes in concentration of PAPS contained in a supernatant of a reaction solution in a PAPS production test.

DESCRIPTION OF EMBODIMENTS

Transformant

A method for producing a sulfated polysaccharide of the present invention is characterized in that a step of 1) supply/regeneration of PAPS is performed by a reaction using bacterial cells. In the method of the present invention, preferably, at least one of the steps of 2) C5-epimerization, 3) 2-O-sulfation, 4) 6-O-sulfation, and 5) 3-O-sulfation is also performed by a reaction using bacterial cells. Hereinafter, transformants (a) to (e) used in each reaction will be described.

Transformant (a): Supply/regeneration of PAPS

In the method for producing a sulfated polysaccharide of the present invention, supply/regeneration of PAPS is performed using a transformant (a) of a microorganism belonging to the genus *Corynebacterium*, comprising at least a gene encoding an ATP sulfurylase and a gene encoding an APS kinase which are introduced thereinto in an expressible manner, or a treated matter of the transformant (a).

Examples of bacterial species of the genus *Corynebacterium* include *Corynebacterium ammoniagenes*, *Corynebacterium acetoacidophilum*, *Corynebacterium acetoglutamicum*, *Corynebacterium alkanolyticum*, *Corynebacterium callunae*, *Corynebacterium crenatum*, *Corynebacterium glutamicum*, *Corynebacterium lilium*, *Corynebacterium melassecola*, *Corynebacterium thermoaminogenes* (*Corynebacterium efficiens*), and *Corynebacterium herculis*.

Examples of strains of the genus *Corynebacterium* include *Corynebacterium ammoniagenes* (*Corynebacterium stationis*) ATCC 6871 and ATCC 6872, *Corynebacterium acetoacidophilum* ATCC 13870, *Corynebacterium acetoglutamicum* ATCC 15806, *Corynebacterium alkanolyticum* ATCC 21511, *Corynebacterium callunae* ATCC 15991, *Corynebacterium crenatum* AS1.542, *Corynebacterium glutamicum* ATCC 13020, ATCC 13032, ATCC 13060, ATCC 13869, and FERM BP-734, *Corynebacterium lilium* ATCC 15990, *Corynebacterium melassecola* ATCC 17965, *Corynebacterium efficiens* (*Corynebacterium thermoaminogenes*) AJ12340 (FERM BP-1539), *Corynebacterium herculis* ATCC 13868, *Brevibacterium divaricatum* (*Corynebacterium glutamicum*) ATCC 14020, *Brevibacterium flavum* (*Corynebacterium glutamicum*) ATCC 13826, ATCC 14067, and AJ12418 (FERM BP-2205), and *Brevibacterium lactofermentum* (*Corynebacterium glutamicum*) ATCC 13869.

Bacteria belonging to the genus *Corynebacterium* also include bacteria that were conventionally classified into the genus *Brevibacterium* but are now integrated into the genus *Corynebacterium* (Int. J. Syst. Bacteriol., 41, 255 (1991)). In addition, *Corynebacterium stationis* also includes bacteria that were conventionally classified as *Corynebacterium ammoniagenes* but are now reclassified as *Corynebacterium stationis* by 16S rRNA nucleotide sequence analysis or the like [Int. J Syst. Evol. Microbiol., 60, 874-879 (2010)].

These strains are available from, for example, the American Type Culture Collection (address: 12301 Parklawn Drive, Rockville, Maryland 20852, P.O. Box 1549, Manassas, VA 20108, United States of America). That is, a registration number is given to each strain, and the strains can be obtained using this registration number (refer to www.atcc.org/). A registration number corresponding to each strain is described in the catalog of the American Type Culture Collection. In addition, these strains are available from, for example, a depository in which each strain is deposited. The bacterium of the genus *Corynebacterium* may be a wild-type strain, a mutant strain thereof, or an artificial recombinant.

In the present invention, a gene encoding an ATP sulfurylase and a gene encoding an APS kinase are introduced into the bacterium of the genus *Corynebacterium* in an expressible manner.

The ATP sulfurylase generates adenosine 5'-phosphosulfate (APS) from sulfate by the following reaction formula.

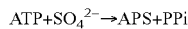 [Chem. 1]

(In the above formula, ATP represents adenosine 5'-triphosphate.)

One aspect of the ATP sulfurylase is MET3. The origin of the ATP sulfurylase is not particularly limited, and examples thereof include ATP sulfurylases derived from *Saccharomyces cerevisiae*, *Candida albicans*, *Shizosaccharomyces pombe*, *Yarrowia lipolytica*, *Neurospora crassa*, *Penicillium chrysogenum*, *Kluyveromyces lactis*, *Fusarium fujikuroi*, *Aspergillus oryzae*, or *Ashbya gossypii*, and among them, an ATP sulfurylase derived from *Saccharomyces cerevisiae* is preferable.

Examples of the gene encoding the ATP sulfurylase include the nucleotide sequence shown in SEQ ID NO: 22. Examples thereof further include a DNA which encodes a polypeptide having an ATP sulfurylase activity, and comprises a nucleotide sequence that is preferably 80% or more, more preferably 90% or more, even more preferably 95% or more, and particularly preferably 98% or more identical to the nucleotide sequence shown in SEQ ID NO: 22; and a DNA which encodes a polypeptide having an ATP sulfurylase activity, and comprises a nucleotide sequence that hybridizes under stringent conditions with the nucleotide sequence shown in SEQ ID NO: 22 or a nucleotide sequence complementary to the above nucleotide sequence. The term "stringent conditions" refers to conditions under which so-called specific hybrids are formed and non-specific hybrids are not formed. Examples thereof include conditions under which DNAs identical to each other at a higher level, for example, DNAs that are 80% or more, preferably 90% or more, more preferably 95% or more, even more preferably 97% or more, and particularly preferably 99% or more identical to each other hybridize with each other, and DNAs identical to each other at a lower level do not hybridize with each other; or conditions, which are conditions for washing in a normal Southern hybridization, in which washing is performed once, preferably two to three times at a salt concentration and a temperature corresponding to 60 degrees C., 1×SSC, and 0.1% SDS, preferably 60 degrees C., 0.1×SSC, and 0.1% SDS, and more preferably 68 degrees C., 0.1×SSC, and 0.1% SDS.

An ATP sulfurylase activity in a transformant is checked by an increase in ATP sulfurylase activity values in a cell extraction liquid of the transformant. The ATP sulfurylase activity can be checked by a method described in the literature [Medina D C et al., Temperature effects on the allosteric transition of ATP sulfurylase from *Penicillium chrysogenum*. Arch. Biochem. Biophys. 1; 393 (1): 51-60 (2001)].

Numerical values regarding identity in the present invention may be numerical values calculated using a homology search program known to those skilled in the art unless otherwise specified. Examples of the numerical values for nucleotide sequences include numerical values calculated using default parameters in BLAST [J. Mol. Biol., 215, 403 (1990)], and examples of the numerical values for amino acid sequences include numerical values calculated using default parameters in BLAST2 [Nucleic Acids Res., 25, 3389 (1997), Genome Res., 7, 649 (1997), www.ncbi.nlm.nih.gov/Education/BLASTinfo/information3.htmL].

The APS kinase generates PAPS from APS according to the following reaction formula.

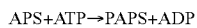 [Chem. 2]

(In the above formula, ADP represents adenosine 5'-diphosphate.)

One aspect of the APS kinase includes MET14. The origin of the APS kinase is not particularly limited, and examples thereof include APS kinases derived from *Saccharomyces cerevisiae*, *Candida albicans*, *Shizosaccharomyces pombe*,

*Yarrowia lipolytica*, *Neurospora crassa*, *Penicillium chrysogenum*, *Kluyveromyces lactis*, *Fusarium fujikuroi*, *Aspergillus oryzae*, or *Ashbya gossypii*, and among them, an APS kinase derived from *Saccharomyces cerevisiae* is preferable.

Examples of the gene encoding the APS kinase include the nucleotide sequence shown in SEQ ID NO: 23. Examples thereof further include a DNA which encodes a polypeptide having an APS kinase activity, and comprises a nucleotide sequence that is preferably 80% or more, more preferably 90% or more, even more preferably 95% or more, and particularly preferably 98% or more identical to the nucleotide sequence shown in SEQ ID NO: 23; and a DNA which encodes a polypeptide having an APS kinase activity, and comprises a nucleotide sequence that hybridizes under stringent conditions with the nucleotide sequence shown in SEQ ID NO: 23 or a nucleotide sequence complementary to the above nucleotide sequence.

An APS kinase activity in a transformant is checked by an increase in APS kinase activity values in a cell extraction liquid of the transformant. The APS kinase activity can be checked by a method described in the literature [Renosto F. et al., Adenosine 5'-phosphosulfate kinase from *Penicillium chrysogenum*. Purification and kinetic characterization. J. Biol. Chem. 259 (4): 2113-2123 (1984)].

Introduction of the gene encoding the ATP sulfurylase and the gene encoding the APS kinase into a bacterium of the genus *Corynebacterium* can be carried out by respectively incorporating the above-described DNAs into the chromosome of a host, or by cloning the above-described DNAs into an appropriate plasmid vector that can be amplified in the host and introducing the vector into the host.

A plasmid vector may be any plasmid vector as long as it has a gene that controls the autonomous replication function in bacteria of the genus *Corynebacterium*. Specific examples thereof include pAM330 derived from *Brevibacterium lactofermentum* 2256 [JP-A-S58-67699], [Miwa, K. et al., Cryptic plasmids in glutamic acid-producing bacteria. Agric. Biol. Chem. 48: 2901-2903 (1984)], and [Yamaguchi, R. et al., Determination of the complete nucleotide sequence of the *Brevibacterium lactofermentum* plasmid pAM330 and the analysis of its genetic information. Nucleic Acids Symp. Ser. 16: 265-267 (1985)]; pHM1519 [Miwa, K. et al., Cryptic plasmids in glutamic acid-producing bacteria. Agric. Biol. Chem. 48: 2901-2903 (1984)] and pCRY30 [Kurusu, Y. et al., Identification of plasmid partition function in coryneform bacteria. Appl. Environ. Microbiol. 57: 759-764 (1991)] which are derived from *Corynebacterium glutamicum* ATCC 3058; pCG4 [JP-A-S57-183799] and [Katsumata, R. et al., Protoplast transformation of glutamate-producing bacteria with plasmid DNA. J. Bacteriol., 159: 306-311 (1984)], pAG1, pAG3, pAG14, and pAG50 [JP-A-S62-166890], and pEK0, pEC5, and pEKEx1 [Eikmanns, B. J. et al., A family of *Corynebacterium glutamicum*/*Escherichia coli* shuttle vectors for cloning, controlled gene expression, and promoter probing. Gene, 102: 93-98 (1991)] which are derived from *Corynebacterium glutamicum* T250, and the like.

A promoter may be a promoter derived from a host or a heterologous promoter. Examples thereof include a promoter PgapA of a glyceraldehyde 3-phosphate dehydrogenase A gene (gapA), a promoter Pmdh of a malate dehydrogenase gene (mdh), a promoter PldhA of a lactate dehydrogenase A gene (ldhA), and the like which are derived from *Corynebacterium glutamicum* R.

Examples of the terminator include a rrnB T1T2 terminator of the *Escherichia coli* rRNA operon, a trpA terminator of *Escherichia coli*, a trp terminator of *Brevibacterium lactofermentum*, and the like.

As one aspect of the present invention, a gene expression of an enzyme relating to degradation of PAPS is not attenuated. Examples of the gene of the enzyme relating to the degradation of PAPS include cysQ gene and CP01850 gene. As one aspect of the transformant (a), an expression of at least one gene selected from cysQ gene and CP01850 gene is not attenuated.

Transformant (b): C5-epimerization

In the method for producing a sulfated polysaccharide according to the present invention, C5-epimerization of N-sulfoheparosan is performed using a transformant (b) of a microorganism belonging to prokaryotes, comprising at least a gene encoding a C5-epimerase which is introduced thereinto in an expressible manner, or a treated matter or extract of the transformant (b).

The C5-epimerase is not particularly limited as long as it can catalyze isomerization of glucuronic acid (GlcUA) residues to iduronic acid (IdoA) residues. The C5-epimerase may be derived from any of animals, plants, microorganisms, and the like. For example, a human C5-epimerase can be used as the C5-epimerase.

Examples of the gene encoding the C5-epimerase include the nucleotide sequence shown in SEQ ID NO: 24. Examples thereof further include a DNA which encodes a polypeptide having a C5-epimerase activity, and comprises a nucleotide sequence that is preferably 80% or more, more preferably 90% or more, even more preferably 95% or more, and particularly preferably 98% or more identical to the nucleotide sequence shown in SEQ ID NO: 24 and a DNA which encodes a polypeptide having a C5-epimerase activity, and comprises a nucleotide sequence that hybridizes under stringent conditions with the nucleotide sequence shown in SEQ ID NO: 24 or a nucleotide sequence complementary to the above nucleotide sequence.

A C5-epimerase activity in a transformant is checked by an increase in C5-epimerase activity values in a cell extraction liquid of the transformant. The C5-epimerase activity can be measured by a method described in the literature [Babu P. et al., A rapid, nonradioactive assay for measuring heparan sulfate C-5 epimerase activity using hydrogen/deuterium exchange-mass spectrometry. Methods. Mol. Biol. 1229: 209-219 (2015)].

Hereinafter, a transformant expressing sulfotransferase will be described. In the method for producing a sulfated polysaccharide of the present invention, sulfation is performed using a transformant comprising a gene encoding sulfotransferase, which is introduced thereinto in an expressible manner, or a treated matter or extract of the transformant. In the present invention, the sulfotransferase is not particularly limited as long as it transfers a sulfate group to polysaccharide to produce sulfated polysaccharide. Examples of the sulfotransferase include 2-O-sulfotransferase (2-OST), 6-O-sulfotransferase (6-OST), and 3-O-sulfotransferase (3-OST).

Transformant (c): 2-O-sulfation

In the method for producing a sulfated polysaccharide of the present invention, 2-O-sulfation is performed using a transformant (c) of a microorganism belonging to prokaryotes, comprising at least a gene encoding a 2-O-sulfotransferase (2-OST) which is introduced thereinto in an expressible manner, or a treated matter or extract of the transformant (c).

The 2-OST is not particularly limited as long as it can catalyze sulfation of IdoA residues at the O-2 position. In addition, the 2-OST may be derived from any of animals, plants, microorganisms, and the like. For example, 2-OST derived from a hamster can be used as the 2-OST.

Examples of the gene encoding the 2-OST include the nucleotide sequence shown in SEQ ID NO: 19. Examples thereof further include a DNA which encodes a polypeptide having a 2-OST activity, and comprises a nucleotide sequence that is preferably 80% or more, more preferably 90% or more, even more preferably 95% or more, and particularly preferably 98% or more identical to the nucleotide sequence shown in SEQ ID NO: 19; and a DNA which encodes a polypeptide having a 2-OST activity, and comprises a nucleotide sequence that hybridizes under stringent conditions with the nucleotide sequence shown in SEQ ID NO: 19 or a nucleotide sequence complementary to the above nucleotide sequence.

A 2-OST activity in a transformant is checked by an increase in 2-OST activity values in a cell extraction liquid of the transformant. The 2-OST activity can be checked by a method described in the literature [Zhang J. et al., High cell density cultivation of recombinant *Escherichia coli* strains expressing 2-O-sulfotransferase and C5-epimerase for the production of bioengineered heparin. Appl. Biochem. Biotechnol. 175 (6): 2986-2995 (2015)].

Transformant (d): 6-O-sulfation

In the method for producing a sulfated polysaccharide of the present invention, 6-O-sulfation is performed using a transformant (d) of a microorganism belonging to prokaryotes, comprising at least a gene encoding a 6-O-sulfotransferase (6-OST) which is introduced thereinto in an expressible manner, or a treated matter or extract of the transformant (d).

The 6-OST is not particularly limited as long as it can catalyze sulfation of N-sulfated glucosamine (GlcNS) residues at the O-6 position. The 6-OST may be derived from any of animals, plants, microorganisms, and the like. Examples of 6-OST include 6-OST-1 derived from a hamster and 6-OST-3 derived from a mouse.

Examples of the gene encoding the 6-OST include the nucleotide sequence shown in SEQ ID NO: 25. Examples thereof further include a DNA which encodes a polypeptide having a 6-OST activity, and comprises a nucleotide sequence that is preferably 80% or more, more preferably 90% or more, even more preferably 95% or more, and particularly preferably 98% or more identical to the nucleotide sequence shown in SEQ ID NO: 25; and a DNA which encodes a polypeptide having a 6-OST activity, and comprises a nucleotide sequence that hybridizes under stringent conditions with the nucleotide sequence shown in SEQ ID NO: 25 or a nucleotide sequence complementary to the above nucleotide sequence.

A 6-OST activity in a transformant is checked by an increase in 6-OST activity values in a cell extraction liquid of the transformant. The 6-OST activity can be checked by a method described in the literature [Zhang J. et al., High cell density cultivation of a recombinant *Escherichia coli* strain expressing a 6-O-sulfotransferase for the production of bioengineered heparin. J. Appl. Microbiol. 118 (1): 92-98 (2015)].

Transformant (e): 3-O-sulfation

In the method for producing a sulfated polysaccharide of the present invention, 3-O-sulfation is performed using a transformant (e) of a microorganism belonging to prokaryotes, comprising at least a gene encoding a 3-O-sulfotransferase (3-OST) which is introduced thereinto in an expressible manner, or a treated matter or extract of the transformant (e).

The 3-OST is not particularly limited as long as it can catalyze sulfation of N-sulfated/6-O-sulfated glucosamine residues at the O-3 position. The 3-OST may be derived from any of animals, plants, microorganisms, and the like. For example, 3-OST-1 derived from a mouse can be used as the 3-OST.

Examples of the gene encoding the 3-OST include the nucleotide sequence shown in SEQ ID NO: 26. Examples thereof further include a DNA which encodes a polypeptide having a 3-OST activity, and comprises a nucleotide sequence that is preferably 80% or more, more preferably 90% or more, even more preferably 95% or more, and particularly preferably 98% or more identical to the nucleotide sequence shown in SEQ ID NO: 26; and a DNA which encodes a polypeptide having a 3-OST activity, and comprises a nucleotide sequence that hybridizes under stringent conditions with the nucleotide sequence shown in SEQ ID NO: 26 or a nucleotide sequence complementary to the above nucleotide sequence.

A 3-OST activity in a transformant is checked by an increase in 3-OST activity values in a cell extraction liquid of the transformant. The 3-OST activity can be checked by a method described in the literature [Jin W. et al., Increased soluble heterologous expression of a rat brain 3-O-sulfotransferase 1—A key enzyme for heparin biosynthesis. Protein Expr. Purif. 151:23-29 (2018)].

Microorganism Belonging to Prokaryotes

Microorganisms belonging to prokaryotes used as a host of the transformant in the present invention is not particularly limited as long as it can express a predetermined gene of the present invention. Examples thereof include bacteria such as microorganisms belonging to the genus *Escherichia*, the genus *Serratia*, the genus *Bacillus*, the genus *Corynebacterium*, the genus *Microbacterium*, and the genus *Pseudomonas*, and a bacterium of the genus *Escherichia* are preferably used.

The bacterium belonging to the genus *Escherichia* used in the present invention is not particularly limited, and examples thereof include a bacterium classified into the genus *Escherichia* by a classification known to experts in microbiology. Examples of the bacteria belonging to the genus *Escherichia* include bacteria described in the literature [Backmann, B J 1996. Derivations and Genotypes of some mutant derivatives of *Escherichia coli* K-12, p. 2460-2488. Table 1. In F. D. Neidhardt (ed.), *Escherichia coli* and *Salmonella* Cellular and Molecular Biology/Second Edition, American Society for Microbiology Press, Washington, DC].

Examples of the bacteria belonging to the genus *Escherichia* include *Escherichia coli*. Examples of *Escherichia coli* include *Escherichia coli* K-12 strains such as a W3110 strain (ATCC 27325) and a MG1655 strain (ATCC 47076); an *Escherichia coli* K5 strain (ATCC 23506); *Escherichia coli* B strains such as a BL21 (DE3) strain; an *Escherichia coli* Nissle 1917 strain (DSM 6601); and derivative strains thereof.

These strains are available from, for example, the American Type Culture Collection (address: 12301 Parklawn Drive, Rockville, Maryland 20852, P.O. Box 1549, Manassas, VA 20108, United States of America). That is, a registration number is given to each strain, and the strains can be obtained using this registration number (refer to www.atcc.org/). A registration number corresponding to each strain is described in the catalog of the American Type Culture Collection. In addition, the BL21 (DE3) strain is available from, for example, Life Technologies (product number C6000-03).

For the purpose of introducing genes in an expressible manner, it is possible to use a vector that can autonomously replicate in a host as a vector used for transformation of a microorganism belonging to prokaryotes. The vector is preferably a multicopy vector. In addition, the vector preferably has a marker such as an antibiotic resistance gene or another gene described in the literature [Karl Friehs, Plasmid Copy Number and Plasmid Stability, Adv Biochem Engin/Biotechnol 86: 47-82 (2004)] in order to select a transformant. Furthermore, the vector may have a promoter or a terminator in order to express an inserted gene. Examples of the vector include a vector derived from a bacterial plasmid, a vector derived from a yeast plasmid, a vector derived from a bacteriophage, a cosmid, a phagemid, and the like.

Specific examples of the vector capable of autonomous replication in bacteria of the genus *Escherichia coli* include pUC19, pUC18, pHSG299, pHSG399, pHSG398, pBR322, and pSTV29 (all from Takara Bio Inc.), pACYC184 and pMW219 (Nippon Gene), pTrc99A (Pharmacia), a pPROK vector (Clontech), pKK233-2 (Clontech), a pET vector (Novagen), a pQE vector (Qiagen), and a broad host range vector RSF1010.

A promoter may be a promoter derived from a host or a heterologous promoter. The promoter may be an intrinsic promoter of a gene to be introduced or a promoter of other genes.

Examples of the terminator include a T7 terminator, a T4 terminator, an fd phage terminator, a tet terminator, and a trpA terminator.

In the above-mentioned transformants (b) to (e), two or more of genes that have been introduced into a microorganism belonging to prokaryotes may be introduced into one transformant. More specifically, for example, the gene encoding the C5-epimerase and the gene encoding the 2-O-sulfotransferase may be introduced into one microorganism belonging to prokaryotes to form one transformant.

Treated Matter of Transformant

The treated matter of the transformant in the present invention refers to a matter in which a cell plasma membrane of a bacterial cell is permeable. In the present invention, when a cell plasma membrane is referred to be substance-permeable, it means that various small (ions and the like) and large (proteins and the like) molecules penetrate through the cell membrane by diffusion and thereby can freely enter and leave the cell membrane. The treated matter of the transformant in the present invention is preferably a quiescent bacterial cell that has lost its growth ability due to treatment for imparting membrane permeability.

Examples of the treated matter of the transformant include a surfactant-treated matter of a bacterial cell that is a transformant, a solvent-treated matter of the bacterial cell, an enzyme-treated matter of the bacterial cell, a treated matter containing live bacterial cells that retain the same function as a culture of the bacterial cell as an enzyme source such as an immobilized product of the bacterial cell, an ultrasonically treated matter of the bacterial cells, and a mechanically ground treated matter of the bacterial cell.

Examples of methods of making a cell plasma membrane substance-permeable include a chemical treatment and a mechanical treatment. In the production method of the present invention, a timing at which the cell plasma membrane of the transformant is made to be substance-permeable is not particularly limited as long as the effects of the present invention are exhibited. A cell plasma membrane of each transformant may be made substance-permeable in advance, or it may be when a reaction is performed by bringing the transformants used in the reaction into contact with each other.

Examples of the chemical treatment include a method using a surfactant, a method using an organic solvent, and a method using an enzyme. As the surfactant, a nonionic surfactant is preferable because its action on proteins or the like is milder (when compared to ionic surfactants). Examples of the surfactant include digitonin, saponin, Triton X100, Triton X114, Tween 20, Tween 80, N,N-bis(3-D-gluconamidopropyl) cholamide [BIGCHAP], N,N-bis(3-D-gluconamidopropyl) deoxycholamide [Deoxy-BIGCHAP], NIKKOLBL-9EX [Polyoxyethylene (9) LaurylEther], octanoyl-N-methylglucamide [MEGA-8], benzalkonium chloride, and the like.

Examples of the organic solvent include benzene, toruene, xylene, other alcohols, and the like. Examples of the enzyme include lysozyme, achromopeptidase, and the like.

Conditions such as concentration, temperature, time, and the like of the treatment with the above-mentioned substances differ depending on the type of cells, and appropriate conditions need to be set to perform a desired analysis, but a general treatment concentration is 10 to 1000 microgram/ml, and more generally 20-200 microgram/ml at a temperature of 2 degrees C. to 37 degrees C. and a time of 1 to 30 minutes.

Examples of the mechanical treatment include an ultrasonic treatment and a mechanical grinding treatment.

Extract of Transformant

Examples of the extract of the transformant in the present invention include a crude enzyme extract obtained from a bacterial cell that is a transformant, a purified enzyme obtained from a bacterial cell treated as above (chemically or mechanically for example), a concentrate of a culture obtained by culturing the above-described transformant or the treated matter thereof, and a dried product of the culture. Examples of the extract of the transformant also include bacterial cells obtained by centrifuging or filtering the culture, dried bacterial cells, and freeze-dried bacterial cells.

Method of Transformation and Method of Culturing Transformant

Known transformation methods can be used without limitation. Examples of such known methods include a calcium chloride/rubidium chloride method, a calcium phosphate method, DEAE-dextran mediated transfection, an electric pulse method, and the like. Among them, the electric pulse method is suitable for coryneform bacteria, and the electric pulse method can be performed by a known method [Kurusu, Y. et al., Electroporation-transformation system for Coryneform bacteria by auxotrophic complementation. Agric Biol. Chem. 54: 443-447 (1990)].

It is preferable that the transformant be grown by culturing using a medium generally used for culturing a microorganism prior to each reaction. As the medium, it is possible to generally use a natural medium or a synthetic medium containing a carbon source, a nitrogen source, inorganic salts, and other nutritional substances.

The carbon source can be an ATP source. Examples of the carbon source include carbohydrates or sugar alcohols such as glucose, fructose, sucrose, mannose, maltose, mannitol, xylose, arabinose, galactose, starch, molasses, sorbitol, and glycerin; organic acids such as acetic acid, citric acid, lactic acid, fumaric acid, maleic acid, and gluconic acid; and alcohols such as ethanol and propanol. As the carbon source, one kind may be used alone, or two or more kinds thereof may be mixed. Generally, it is sufficient for a concentration of these carbon sources in a medium be about 0.1 to 10 (w/v %).

Examples of the nitrogen source include inorganic or organic ammonium compounds such as ammonium chloride, ammonium sulfate, ammonium nitrate, and ammonium acetate, urea, aqueous ammonia, sodium nitrate, potassium nitrate, and the like. In addition, it is also possible to use corn steep liquor, meat extract, peptone, NZ-amine, protein hydrolyzate, nitrogen-containing organic compounds such as amino acids, and the like. As the nitrogen source, one kind may be used alone, or two or more kinds thereof may be mixed and used. A concentration of the nitrogen source in a medium varies depending on a nitrogen compound used, but it is generally about 0.1 to 10 (w/v %).

Examples of the inorganic salt include monobasic potassium phosphate, dibasic potassium phosphate, ferrous nitrate, sodium chloride, calcium carbonate, and the like in addition to sulfate ion sources such as magnesium sulfate, manganese sulfate, zinc sulfate, and cobalt sulfate. As the inorganic salts, one kind may be used alone, or two or more kinds thereof may be mixed and used. A concentration of the inorganic salts in a medium varies depending on an inorganic salt used, but it is generally about 0.01 to 1 (w/v %).

Examples of the nutritional substance include meat extract, peptone, polypeptone, yeast extract, dried yeast, corn steep liquor, skim milk powder, defatted soy hydrochloride hydrolyzate, extracts of animal and plant or microbial bacterial cells and their decomposed products, and the like, and a concentration thereof is generally about 0.1 to 10 (w/v %). In addition, vitamins can be added if necessary. Examples of the vitamins include biotin, thiamine (vitamin B1), pyridoxine (vitamin B6), pantothenic acid, inositol, nicotinic acid, and the like. A pH of a medium is preferably about 6 to 8.

Preferable examples of culture media for a microorganism include an A medium [Inui, M. et al., Metabolic analysis of *Corynebacterium glutamicum* during lactate and succinate productions under oxygen deprivation conditions. J. Mol. Microbiol. Biotechnol. 7:182-196 (2004)], a BT medium [Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)], and the like. As specific culture conditions, for example, a culture temperature is about 15 degrees C. to 45 degrees C., and a culture time is about 1 to 7 days.

Method for Producing Sulfated Polysaccharide

One aspect of the method for producing a sulfated polysaccharide according to the present invention is a method for producing a sulfated polysaccharide, the method comprising generating a sulfated polysaccharide by incorporating, in the reaction solution in the presence of ATP or the ATP source, the sulfate ion source, and N-sulfoheparosan, the transformant (a) or the treated matter thereof, and at least one selected from the transformants (b) to (e) or the treated matters or extracts thereof.

As one aspect of the method for producing a sulfated polysaccharide according to the present invention, examples thereof include a method for producing a sulfated polysaccharide, the method comprising generating a sulfated polysaccharide by using the reaction solution containing the transformant (a) or the treated matter thereof, and the transformants (b) to (e) or the treated matters or extracts thereof, in the presence of ATP or the ATP source, the sulfate ion source, and N-sulfoheparosan.

In addition, one aspect of the method for producing a sulfated polysaccharide according to the present invention is a method for producing a sulfated polysaccharide, the method comprising generating a sulfated polysaccharide by incorporating at least one selected from the transformants (b) to (e) or the treated matters or extracts thereof in the reaction solution in the presence of PAPS and N-sulfoheparosan.

In the production method of the present invention, each transformant may be initially added to the reaction solution, may be sequentially added thereto, or may be initially and sequentially added thereto. Specific examples of aspects of initially adding each transformant to the reaction solution include an aspect in which sulfated polysaccharides are generated by initially adding the transformant (a) or the treated matter thereof, and the transformants (b) to (e) or the treated matters or extracts thereof to the reaction solution in the presence of ATP or the ATP source, the sulfate ion source, and N-sulfoheparosan.

In the method for producing a sulfated polysaccharide of the present invention, using the transformant (a) or the treated matter thereof and the transformants (b) to (e) or the treated matters or extract thereof, it is possible to perform 1) supply/regeneration of PAPS with the transformant (a) or the treated matter thereof, 2) C5-epimerization with the transformant (b) or the treated matter or extract thereof, 3) 2-O-sulfation with the transformant (c) or the treated matter or extract thereof, 4) 6-O-sulfation with the transformant (d) or the treated matter or extract thereof, and 5) 3-O-sulfation with the transformant (e) or the treated matter or extract thereof.

Hereinafter, each of the steps will be described separately, but the order of 2) C5-epimerization, 3) 2-O-sulfation, 4) 6-O-sulfation, and 5) 3-O-sulfation is not particularly limited as long as desired sulfated polysaccharides can be obtained.

In addition, hereinafter, each reaction of 1) supply/regeneration of PAPS, 2) C5-epimerization, 3) 2-O-sulfation, 4) 6-O-sulfation, and 5) 3-O-sulfation will be described separately, but two or more of these reactions may be performed at the same time. For example, these reactions may be performed at the same time using a reaction solution containing all the transformant (a) or the treated matter thereof and the transformants (b) to (e) or the treated matters or extracts thereof.

Examples of the sulfated polysaccharide produced by the method for producing a sulfated polysaccharide of the present invention include heparin.

Supply/regeneration of PAPS

The method for producing a sulfated polysaccharide of the present invention is characterized by comprising the following steps (1-1) and (1-2):

(1-1) preparing a transformant (a) of a bacterium of the genus *Corynebacterium*, comprising at least a gene encoding an ATP sulfurylase and a gene encoding an APS kinase which are introduced thereinto in an expressible manner, or a treated matter of the transformant (a); and (1-2) conducting a reaction for producing PAPS by using a reaction solution containing ATP or an ATP source, a sulfate ion source, and the transformant (a) or the treated matter thereof.

The ATP sulfurylase and the APS kinase expressed by the transformant (a) or the treated matter thereof react with ATP or an ATP source and a sulfate ion source in the transformant (a) or the treated matter thereof, and thereby PAPS is produced. The PAPS functions as a donor of a sulfate group in the production of sulfated polysaccharides. In addition, PAPS produced by the transformant (a) or the treated matter thereof is used in the method for producing a sulfated polysaccharide, and thereby PAP is obtained. PAPS can be produced from this PAP by the transformant (a) or the treated matter thereof. Accordingly, PAPS can be supplied/regenerated by incorporating the transformant (a) or the treated matter thereof in the reaction solution.

C5-epimerization

The method for producing a sulfated polysaccharide of the present invention preferably comprises the following steps (2-1) and (2-2):

(2-1) preparing a transformant (b) of a microorganism belonging to prokaryotes, comprising at least a gene encoding a C5-epimerase which is introduced thereinto in an expressible manner, or a treated matter or extract of the transformant (b); and (2-2) conducting C5-epimerization by incorporating the transformant (b) or the treated matter or extract thereof in the reaction solution in the presence of N-sulfoheparosan.

In the step (2-2), C5-epimerization of N-sulfoheparosan is carried out by the transformant (b) expressing the C5-epimerase or the treated matter or extract thereof.

2-O-sulfation

The method for producing a sulfated polysaccharide of the present invention preferably comprises the following steps (3-1) and (3-2):

(3-1) preparing a transformant (c) of a microorganism belonging to prokaryotes, comprising at least a gene encoding a 2-O-sulfotransferase which is introduced in an expressible manner, or a treated matter or extract of the transformant (c); and (3-2) conducting 2-O-sulfation by incorporating the transformant (c) or the treated matter or extract thereof in the reaction solution in the presence of N-sulfoheparosan.

In the step (3-2), 2-O-sulfation of N-sulfoheparosan is carried out by the transformant (c) expressing the 2-O-sulfotransferase or the treated matter or extract thereof using PAPS produced by the transformant (a) or the treated matter thereof as a donor of a sulfate group.

When the sulfated polysaccharide produced in the step (2-2) exists in the reaction solution, the 2-O-sulfation of the sulfated polysaccharide produced in the step is conducted. For example, when N-sulfoheparosan with C5-epimerization exists, the 2-O-sulfation of the N-sulfoheparosan with C5-epimerization is conducted.

The above-mentioned C5-epimerization and 2-O-sulfation may be carried out at the same time. That is, one aspect of the method for producing a sulfated polysaccharide of the present invention preferably comprises the following steps (3'-1) to (3'-3):

(3'-1) preparing a transformant (b) of a microorganism belonging to prokaryotes, comprising at least a gene encoding a C5-epimerase which is introduced thereinto in an expressible manner, or a treated matter or extract of the transformant (b);

(3'-2) preparing a transformant (c) of a microorganism belonging to prokaryotes, comprising at least a gene encoding a 2-O-sulfotransferase which is introduced thereinto in an expressible manner, or a treated matter or extract of the transformant (c); and (3'-3) conducting C5-epimerization and 2-O-sulfation by incorporating the transformant (b) or the treated matter or extract thereof, and the transformant (c) or the treated matter or extract thereof in the reaction solution in the presence of N-sulfoheparosan.

6-O-sulfation

The method for producing a sulfated polysaccharide of the present invention preferably comprises the following steps (4-1) and (4-2):

(4-1) preparing a transformant (d) of a microorganism belonging to prokaryotes, comprising at least a gene encoding a 6-O-sulfotransferase which is introduced thereinto in an expressible manner, or a treated matter or extract of the transformant (d); and (4-2) conducting 6-O-sulfation by incorporating the transformant (d) or the treated matter or extract thereof in the reaction solution in the presence of N-sulfoheparosan.

In the step (4-2), 6-O-sulfation of N-sulfoheparosan is carried out by the transformant (d) expressing the 6-O-sulfotransferase or the treated matter or extract thereof using PAPS produced by the transformant (a) or the treated matter thereof as a donor of a sulfate group.

When the sulfated polysaccharide produced in the step (2-2), (3-2) or (3'-3) exists in the reaction solution, the 6-O-sulfation of the sulfated polysaccharide produced in the step is conducted.

For example, when N-sulfoheparosan with C5-epimerization exists, the 6-O-sulfation of the N-sulfoheparosan with C5-epimerization is conducted. When N-sulfoheparoson with 2-O-sulfation exists, the 6-O-sulfation of the N-sulfoheparosan with 2-O-sulfation is conducted.

When N-sulfoheparosan with C5-epimerization and 2-O-sulfation exists, the 6-O-sulfation of the N-sulfoheparosan with C5-epimerization and 2-O-sulfation is conducted.

3-O-sulfation

The method for producing a sulfated polysaccharide of the present invention preferably comprises the following steps (5-1) and (5-2):

(5-1) preparing a transformant (e) of a microorganism belonging to prokaryotes, comprising at least a gene encoding a 3-O-sulfotransferase which is introduced thereinto in an expressible manner, or a treated matter or extract of the transformant (e); and (5-2) conducting 3-O-sulfation by incorporating the transformant (e) or the treated matter or extract thereof in the reaction solution in the presence of N-sulfoheparosan.

In the step (5-2), 3-O-sulfation of N-sulfoheparosan is carried out by the transformant (e) expressing the 3-O-sulfotransferase or the treated matter or extract thereof using PAPS produced by the transformant (a) or the treated matter thereof as a donor of a sulfate group.

When the sulfated polysaccharide produced in the step (2-2), (3-2), (3'-3) or (4-2) exists in the reaction solution, the 3-O-sulfation of the sulfated polysaccharide produced in the step is conducted.

For example, when N-sulfoheparosan with C5-epimerization exists, the 3-O-sulfation of the N-sulfoheparosan with C5-epimerization is conducted. When N-sulfoheparoson with 2-O-sulfation exists, the 3-O-sulfation of the N-sulfoheparosan with 2-O-sulfation is conducted. When N-sulfoheparosan with 6-O-sulfation exists, the 3-O-sulfation of the N-sulfoheparosan with 6-O-sulfation is conducted.

When N-sulfoheparosan with C5-epimerization and 2-O-sulfation exists, the 3-O-sulfation of the N-sulfoheparosan with C5-epimerization and 2-O-sulfation is conducted. When N-sulfoheparosan with C5-epimerization and 6-O-sulfation exists, the 3-O-sulfation of the N-sulfoheparosan with C5-epimerization and 6-O-sulfation is conducted. When N-sulfoheparosan with 2-O-sulfation and 6-O-sulfation exists, the 3-O-sulfation of the N-sulfoheparosan with 2-O-sulfation and 6-O-sulfation is conducted.

When N-sulfoheparosan with C5-epimerization, 2-O-sulfation and 6-O-sulfation exists, the 3-O-sulfation of the N-sulfoheparosan with C5-epimerization, 2-O-sulfation and 6-O-sulfation is conducted.

Reaction Conditions

Reaction conditions of the above-mentioned 1) supply/regeneration of PAPS, 2) C5-epimerization, 3) 2-O-sulfation, 4) 6-O-sulfation, and 5) 3-O-sulfation will be described below.

A pH of the reaction solution is preferably about 6 to 8. During the reaction, it is preferable to carry out the reaction using an aqueous solution of ammonia, an aqueous solution of sodium hydroxide, potassium hydroxide, or the like with a pH controller to control a pH of the reaction solution to near neutral, particularly about 7.

A reaction temperature, that is, a survival temperature of the transformant during the reaction is preferably 20 degrees C. to 50 degrees C., and more preferably 25 degrees C. to 47 degrees C. A reaction time is preferably about 1 to 7 days and more preferably about 1 to 3 days. The culture may be any of a batch type, a fed-batch type, and a continuous type. Among them, the batch type is preferable.

An aeration condition reaction may be performed under reduction conditions or microaerobic conditions. The reduction conditions are defined by oxidation-reduction potential of the reaction solution. An oxidation-reduction potential of the reaction solution is preferably about −200 mV to −500 mV and more preferably −250 mV to −500 mV.

A reduction state of the reaction solution can be easily estimated using a resazurin indicator, and can be accurately measured using an oxidation-reduction potentiometer. As a method for preparing a reaction solution under reduction conditions, a known method can be used without limitation.

Specifically, an aqueous solution for a reaction solution under reduction conditions can be obtained by removing a dissolved gas by subjecting distilled water or the like to a heat treatment or a reduced pressure treatment. In addition, an appropriate reducing agent (for example, thioglycolic acid, ascorbic acid, cystine hydrochloride, mercaptoacetic acid, thioacetic acid, glutathione, sodium sulfide, or the like) can be added to prepare an aqueous solution for a reaction solution under reduction conditions. An appropriate combination of these methods is also an effective method for preparing an aqueous solution for a reaction solution under reduction conditions.

In a case where reduction conditions are maintained during the reaction, it is desirable to prevent mixing of oxygen from outside the reaction system as much as possible, and specific examples of such a method include a method in which the reaction system is enclosed with an inert gas such as nitrogen gas or a carbon dioxide gas.

In a case where microaerobic conditions are maintained during the reaction, the reaction can be carried out under conditions in which an aeration rate is set to a low value of 0.5 vvm or the like or a lower value, and a stirring speed is set to a low value of 500 rpm or the like or a lower value. In some cases, the reaction can be performed in combination with a state in which aeration is stopped at an appropriate timing after the start of the reaction, and a degree of anaerobic state is increased under conditions of a stirring speed of 100 rpm or less.

Collection of Sulfated Polysaccharide

The sulfated polysaccharide is produced in the reaction solution by culturing as described above. The sulfated polysaccharide can be collected by recovering the reaction solution, and furthermore, the sulfated polysaccharide can be separated from the reaction solution by a known method. Examples of such known methods include a distillation method, a membrane permeation method, an organic solvent extraction method, and the like.

Preparation of N-sulfoheparosan

N-sulfoheparosan used in the method for producing a sulfated polysaccharide of the present invention is obtained by deacetylating, depolymerizing, and N-sulfating heparosan. Production of heparosan and production of N-sulfoheparosan from heparosan can be carried out by a known method (for example, WO2018/048973).

Examples of the method for producing heparosan include a method comprising culturing a microorganism belonging to prokaryotes having genetic modification of the following (a1) and having a heparosan-producing ability in a medium to produce heparosan in the medium, and collecting heparosan from the medium:
   (a1) a genetic modification that increases an expression level of a kpsS gene.

The microorganism belonging to prokaryotes may further have at least one of the following genetic modifications (a2) and (a3) in addition to (a1):
   (a2) a genetic modification that increases an expression level of at least one gene selected from kfiA, kfiB, kfiC, and kfiD genes; and
   (a3) a genetic modification that causes loss of a function of a yhbJ gene The kpsS gene is a gene encoded by Region I among the gene group of Region I, Region II, and Region III. kpsS is involved in initiation of heparosan synthesis. In heparosan production, kpsS, together with kpsC, plays a role in adding multiple Kdo linkers to phosphatidylglycerol in the inner membrane.

As the kpsS gene, a kpsS gene derived from the genus *Escherichia* is preferable. Specific examples thereof include a kpsS gene of an *Escherichia coli* K5 strain. A nucleotide sequence of the kpsS gene of the *Escherichia coli* K5 strain and an amino acid sequence of the protein encoded by the gene can be obtained from public databases. The kpsS gene of the *Escherichia coli* K5 strain is registered as GenBank accession CAA52659.1.

Examples of the kpsS gene include a DNA having the nucleotide sequence shown in SEQ ID NO: 27, or a DNA having a property of increasing a heparosan-producing ability of a microorganism when an expression level is increased in the microorganism belonging to prokaryotes having a nucleotide sequence 90% or more identical to the nucleotide sequence shown in SEQ ID NO: 27 and having the heparosan-producing ability.

The kfiA, kfiB, kfiC, and kfiD are genes encoded by Region II among the gene group of Region I, Region II, and Region III. As shown in FIG. 2, the kfiA, kfiB, kfiC and kfiD are involved in synthesis of heparosan, and play a role of adding saccharide and thereby synthesizing heparosan.

As the kfiA, kfiB, kfiC or kfiD gene, a kfiA, kfiB, kfiC, or kfiD gene derived from the genus *Escherichia* is preferable. Specific examples thereof include a kfiA, kfiB, kfiC, or kfiD gene of an *Escherichia coli* K5 strain. A nucleotide sequence of the kfiA, kfiB, kfiC, or kfiD gene of the *Escherichia coli* K5 strain and an amino acid sequence of a protein encoded by the gene can be obtained from public databases. The kfiA is registered as GenBank accession CAA54711.1; the kfiB is registered as GenBank accession CAE55824.1; the kfiC is registered as GenBank accession CAA54709.1; and the kfiD is registered as GenBank accession CAA54708.1.

Examples of the kfiA gene include a DNA having the nucleotide sequence shown in SEQ ID NO: 28, or a DNA having a property of increasing a heparosan-producing ability of a microorganism when an expression level is increased in the microorganism belonging to prokaryotes having a nucleotide sequence 90% or more identical to the nucleotide sequence shown in SEQ ID NO: 28 and having the heparosan-producing ability.

Examples of the kfiB gene include a DNA having the nucleotide sequence shown in SEQ ID NO: 29, or a DNA having a property of increasing a heparosan-producing ability of a microorganism when an expression level is increased in the microorganism belonging to prokaryotes having a nucleotide sequence 90% or more identical to the nucleotide sequence shown in SEQ ID NO: 29 and having the heparosan-producing ability.

Examples of the kfiC gene include a DNA having the nucleotide sequence shown in SEQ ID NO: 30, or a DNA having a property of increasing a heparosan-producing ability of a microorganism when an expression level is increased in the microorganism belonging to prokaryotes having a nucleotide sequence 90% or more identical to the nucleotide sequence shown in SEQ ID NO: 30 and having the heparosan-producing ability.

Examples of the kfiD gene include a DNA having the nucleotide sequence shown in SEQ ID NO: 31, or a DNA having a property of increasing a heparosan-producing ability of a microorganism when an expression level is increased in the microorganism belonging to prokaryotes having a nucleotide sequence 90% or more identical to the nucleotide sequence shown in SEQ ID NO: 31 and having the heparosan-producing ability.

FIG. 3 shows a schematic diagram of a heparosan biosynthetic pathway. GlmS is the first enzyme in an UDP-N-acetylglucosamine supply pathway that is a precursor of heparosan and is an enzyme that catalyzes reaction from fructose-6-phosphate to glucosamine-6-phosphate. YhbJ is an enzyme that negatively controls GlmS.

As the yhbJ gene, a yhbJ gene derived from the genus *Escherichia* is preferable. Specific examples thereof include a yhbJ gene of an *Escherichia coli* K-12 strain. A nucleotide sequence of the yhbJ gene of the *Escherichia coli* K-12 strain and an amino acid sequence of a protein encoded by the gene can be obtained from public databases. The yhbJ gene of the *Escherichia coli* K-12 strain is registered as GenBank accession BAE77249.1.

Examples of the yhbJ gene include a DNA having the nucleotide sequence shown in SEQ ID NO: 32, or a DNA having a property of increasing a heparosan-producing ability of a microorganism when an expression level is decreased in the microorganism belonging to prokaryotes having a nucleotide sequence 90% or more identical to the nucleotide sequence shown in SEQ ID NO: 32 and having the heparosan-producing ability.

Each of the genes in (a1) to (a3) above can be easily obtained from public databases by, for example, a BLAST search or a FASTA search using a nucleotide sequence of each gene described above. In addition, a homologue of each gene can be obtained by, for example, PCR using a chromosome of a microorganism such as a bacterium as a template and using an oligonucleotide produced based on these known gene sequences as a primer.

Each of the genes in (a1) to (a3) above may be a variant of the genes as long as original functions (for example, an activity or a property) of a protein encoded by the genes are maintained. Whether or not a protein encoded by a variant of the genes maintains its original function can be checked; specifically, for example, when the original function is to improve a heparosan-producing ability, by introducing the variant of the gene into a microorganism belonging to prokaryotes having the heparosan-producing ability.

Variants of each of the genes in (a1) to (a3) above can be obtained according to a site-directed mutagenesis method by modifying an encoding region of a gene such that amino acid residues at specific positions of an encoded protein are substituted, deleted, inserted, or added. In addition, variants of each of the genes in (a1) to (a3) above can also be obtained by, for example, mutation treatment.

As long as their original functions are maintained, each of the genes (a1) to (a3) above may be genes encoding a protein having an amino acid sequence in which one or several amino acids at one or several positions are substituted, deleted, inserted, or added. For example, in an encoded protein, its N-terminus and/or C-terminus may be extended or shortened. The phrase "one or several" differs depending on the position and type of an amino acid residue in the three-dimensional structure of a protein. Specific examples thereof include 1 to 50, 1 to 40, 1 to 30, and it is preferably 1 to 20, more preferably 1 to 10, even more preferably 1 to 5, and particularly preferably 1 to 3.

The substitution, deletion, insertion, or addition of one or several amino acids as described above is a conservative mutation that maintains a function of a protein normally. Representatives of conservative mutations are a conservative substitution. The conservative substitution is a mutation in which substitution occurs between Phe, Trp, and Tyr in a case where a substitution site is an aromatic amino acid, substitution occurs between Leu, Ile, and Val in a case where a substitution site is a hydrophobic amino acid, substitution occurs between Gln and Asn in a case where a substitution site is a polar amino acid, substitution occurs between Lys, Arg, and His in a case where a substitution site is a basic amino acid, substitution occurs between Asp and Glu in a case where a substitution site is an acidic amino acid, and substitution occurs between Ser and Thr in a case where a substitution site is an amino acid having hydroxyl groups. Specific examples of substitutions considered as a conservative substitution include substitution of Ala with Ser or Thr; substitution of Arg with Gln, His, or Lys; substitution of Asn with Glu, Gln, Lys, His, or Asp; substitution of Asp with Asn, Glu, or Gln; substitution of Cys with Ser or Ala; Substitution of Gln with Asn, Glu, Lys, His, Asp, or Arg; substitution of Glu with Gly, Asn, Gln, Lys, or Asp; substitution of Gly with Pro; substitution of His with Asn, Lys, Gln, Arg, or Tyr; substitution of Ile with Leu, Met, Val, or Phe; substitution of Leu with Ile, Met, Val, or Phe; substitution of Lys with Asn, Glu, Gln, His, or Arg; substitution of Met with Ile, Leu, Val, or Phe; substitution of Phe with Trp, Tyr, Met, Ile, or Leu; substitution of Ser with Thr or Ala; substitution of Thr with Ser or Ala; substitution of Trp with Phe or Tyr; substitution of Tyr with His, Phe, or Trp; and substitution of Val with Met, Ile, or Leu. In addition, the substitutions, deletions, insertions, additions of amino acids as described above, inversions thereof, and the like include substitutions, deletions, insertions, and additions, inversions, and the like which are caused by mutations (mutants or variants) that occur naturally such as mutations based on individual differences or species differences in an organism from which a gene is derived.

In addition, as long as their original functions are maintained, each of the genes in (a1) to (a3) above may be genes encoding a protein that is 80% or more, preferably 90% or more, more preferably 95% or more, even more preferably 97% or more, and particularly preferably 99% or more identical to the entire amino acid sequence.

In addition, as long as their original functions are maintained, each of the genes in (a1) to (a3) above may be a DNA that hybridizes, under stringent conditions, with a probe that can be prepared from known gene sequences, such as a sequence complementary to the whole or a part of the nucleotide sequence. The term "stringent conditions" refers to conditions under which so-called specific hybrids are formed and non-specific hybrids are not formed. Examples thereof include conditions under which DNAs identical to each other at a higher level, for example, DNAs that are 80% or more, preferably 90% or more, more preferably 95% or more, even more preferably 97% or more, and particularly preferably 99% or more identical to each other hybridize with each other, and DNAs identical to each other at a lower level do not hybridize with each other; or conditions, which are conditions for washing in a normal Southern hybridization, in which washing is performed once, preferably two to three times at a salt concentration and a temperature corresponding to 60 degrees C., 1×SSC, and 0.1% SDS, preferably 60 degrees C., 0.1×SSC, and 0.1% SDS, and more preferably 68 degrees C., 0.1×SSC, and 0.1% SDS.

The probe used for the above hybridization may be a part of the complementary sequence of each gene. Such a probe can be produced by PCR using an oligonucleotide produced based on a known gene sequence as a primer and using a DNA fragment containing each of the genes in (a1) to (a3) above as a template. For example, a DNA fragment having a length of about 300 bp can be used as a probe. In a case where a DNA fragment having a length of about 300 bp is used as a probe, examples of conditions for washing in hybridization include conditions of 50 degrees C., 2×SSC, and 0.1% SDS.

In addition, because codon degeneracy differs depending on hosts, each of the genes in (a1) to (a3) above may be genes obtained by replacing any codon with an equivalent codon as long as their original functions are maintained. For example, genes in Tables 1 to 3 may be modified so that they have optimal codons depending on frequency of codon usage of a host used.

Examples of the mutation treatment include a method of in vitro treating a DNA molecule having a nucleotide sequence of each of the genes in (a1) to (a3) above with hydroxylamine or the like; a method of treating microorganisms carrying each of the genes in (a1) to (a3) above with X-rays, ultraviolet rays, or a mutagen such as N-methyl-N'-nitro-N-nitrosoguanidine (NTG), ethyl methanesulfonate (EMS), and methyl methanesulfonate (MMS); and the like.

Genetic Modification to Increase Gene Expression

The phrase "increase in gene expression" means that expression of a gene is elevated as compared to that of an unmodified strain. Examples of one aspect of increasing expression of a gene include an aspect in which expression of a gene is preferably increased 1.5-fold or more, is more preferably increased 2-fold or more, and is even more preferably increased 3-fold or more, as compared to that of an unmodified strain.

In addition, the phrase "gene expression is increased" means not only an increase in expression of a target gene in a strain in which the target gene is originally expressed, but also means that a target gene is expressed in a strain in which the target gene is originally not expressed. That is, the phrase "gene expression is increased" includes, for example, a case in which a target gene is introduced into a strain not having the target gene, and the target gene is expressed therein. Furthermore, the phrase "gene expression is increased" is also referred to as the phrases "gene expression is enhanced" or "gene expression is elevated."

An increase in gene expression can be achieved by, for example, increasing the copy number of the gene. Increasing the copy number of the gene can be achieved by introducing the gene into the chromosome of a host. Introduction of the gene into the chromosome can be performed using, for example, homologous recombination (Miller I, J. H. Experiments in Molecular Genetics, 1972, Cold Spring Harbor Laboratory). Only one copy of the gene may be introduced, or two or more copies thereof may be introduced.

For example, multiple copies of a gene can be introduced into the chromosome by performing homologous recombination while targeting a sequence having multiple copies on the chromosome. Examples of the sequence having multiple copies on the chromosome include a repetitive DNA sequence (a repetitive DNA), and inverted repeats present at both ends of a transposon.

Alternatively, homologous recombination may be performed while targeting an appropriate sequence on the chromosome, such as a gene unnecessary for production of a target substance. The homologous recombination can be performed by, for example, a method using a linear DNA, a method using a plasmid containing a temperature-sensitive replication origin, a method using a plasmid capable of conjugative transfer, a method using a suicide vector not having a replication origin that functions in a host, or a transduction method using phage. In addition, a gene can also be randomly introduced into the chromosome using a transposon or Mini-Mu (JP-A-H2-109985).

Whether a target gene has been introduced into the chromosome can be checked by Southern hybridization using a probe having a sequence complementary to all or a part of the gene, PCR using a primer produced based on a sequence of the gene, or the like.

In addition, the copy number of gene can also be increased by introducing a vector containing the gene into a host. For example, it is possible to increase the copy number of the gene by constructing an expression vector for the gene by ligating a DNA fragment containing the target gene to a vector that functions in a host, and transforming the host with the expression vector. The DNA fragment containing the target gene can be obtained by, for example, PCR using a genomic DNA of a microorganism having the target gene as a template. A transformation method is not particularly limited, and a conventionally known method can be used.

As the vector, a vector that can autonomously replicate in a host cell can be used. The vector is preferably a multicopy vector. In addition, the vector preferably has a marker such as an antibiotic resistance gene or another gene described in the literature [Karl Friehs, Plasmid Copy Number and Plasmid Stability, Adv Biochem Engin/Biotechnol 86: 47-82 (2004)] in order to select a transformant. Furthermore, the vector may have a promoter or a terminator in order to express an inserted gene. Examples of the vector include a vector derived from a bacterial plasmid, a vector derived from a yeast plasmid, a vector derived from a bacteriophage, a cosmid, a phagemid, and the like.

Specific examples of vectors capable of autonomous replication in bacteria of Enterobacteriaceae such as *Escherichia coli* include pUC19, pUC18, pHSG299, pHSG399, pHSG398, pBR322, and pSTV29 (all from Takara Bio Inc.), pACYC184 and pMW219 (Nippon Gene), pTrc99A (Pharmacia), a pPROK vector (Clontech), pKK233-2 (Clontech), a pET vector (Novagen), a pQE vector (Qiagen), and a broad host range vector RSF1010.

In a case of introducing a gene, it is sufficient for the gene be retained in a microorganism belonging to prokaryotes having the genetic modification in the present invention. Specifically, it is sufficient for the gene be introduced such that it is expressed upon control of a promoter sequence that functions in the bacterium of the present invention. A promoter may be a promoter derived from a host or a heterologous promoter. The promoter may be an intrinsic promoter of a gene to be introduced or a promoter of other genes. As the promoter, for example, a stronger promoter which will be described later may be used.

A terminator for terminating transcription can be disposed downstream of a gene. The terminator is not particularly limited as long as it functions in the bacterium of the present invention. The terminator may be a terminator derived from a host or a heterologous terminator. The terminator may be a terminator specific to a gene to be introduced, or may be a terminator of other genes. Specific examples of terminators include a T7 terminator, a T4 terminator, an fd phage terminator, a tet terminator, and a trpA terminator.

Vectors, promoters, and terminators that can be used in various microorganisms are described in detail in, for example, "Basic Lecture 8 on Microbiology, Gene Engineering, KYORITSU SHUPPAN, 1987," and these can be used.

In addition, in a case where two or more genes are introduced, it is sufficient for each gene be retained in the bacterium of the present invention in an expressible manner. For example, each gene may all be retained on a single expression vector, or all may be retained on a chromosome. Furthermore, each gene may be separately retained on a plurality of expression vectors, or may be separately retained on a single or a plurality of expression vectors and on a chromosome. Furthermore, two or more genes may form an operon and be introduced. Examples of the "cases where two or more genes are introduced" include a case of introducing genes respectively encoding two or more enzymes, a case of introducing genes respectively encoding two or more subunits that form a single enzyme, and combinations thereof.

A gene to be introduced is not particularly limited as long as it encodes a protein that functions in a host. The gene to be introduced may be a gene derived from a host or a heterologous gene. The gene to be introduced can be obtained by, for example, PCR using primers designed based on a nucleotide sequence of the gene and using genomic DNA of an organism having the gene or a plasmid or the like carrying the gene as a template. In addition, the gene to be introduced may be totally synthesized, for example, based on a nucleotide sequence of the gene [Gene, 60 (1), 115-127 (1987)].

Furthermore, an increase in a gene expression can be achieved by improving transcription efficiency of the gene. Improving transcription efficiency of a gene can be achieved by, for example, replacing a promoter of the gene on the chromosome with a stronger promoter. The "stronger promoter" refers to a promoter that enhances gene transcription over a naturally occurring wild-type promoter.

Examples of the "stronger promoter" include known high expression promoters such as a uspA promoter, a T7 promoter, a trp promoter, a lac promoter, a thr promoter, a tac promoter, a trc promoter, a tet promoter, an araBAD promoter, an rpoH promoter, a PR promoter, and a PL promoter.

In addition, as the stronger promoter, a conventional promoter of a highly active type may be obtained using various reporter genes. For example, an activity of the promoter can be increased by bringing −35 and −10 regions in a promoter region closer to a consensus sequence (WO2000/18935).

Examples of highly-active-type promoters include various tac-like promoters (Katashkina J I et al. Russian Federation Patent application 2006134574) and a pnlp8 promoter (International WO2010/027045). Methods for evaluating promoter strength, and examples of strong promoters are described in known literature [Prokaryotic promoters in biotechnology. Biotechnol. Annu. Rev., 1, 105-128 (1995) and the like].

In addition, an increase in a gene expression level can be achieved by improving translation efficiency of the gene. Improvement in translation efficiency of a gene can be achieved by, for example, replacing a Shine-Dalgarno (SD) sequence (also called a ribosome binding site (RBS)) of the gene on the chromosome with a stronger SD sequence.

The "stronger SD sequence" refers to an SD sequence in which mRNA translation is improved over a naturally occurring wild-type SD sequence. Examples of the stronger SD sequence include the RBS of gene 10 from phage T7 [Olins P. O. et al, Gene, 1988, 73, 227-235]. In addition, substitution, insertion, or deletion of several nucleotides in a spacer region between an RBS and a start codon, particularly in a sequence immediately upstream of the start codon (5'-UTR), is known to significantly affect stability and translation efficiency of mRNA, and therefore, translation efficiency of a gene can be improved by modifying these.

In the present invention, sites that affect expression of a gene, such as a promoter, an SD sequence, and a spacer region between an RBS and a start codon, are also collectively referred to as "expression control regions." The expression control regions can be determined using a gene search software such as a promoter search vector or GENE-TYX. Modification of these expression control regions can be performed by, for example, a method using a temperature-sensitive vector or a Red driven integration method (WO2005/010175).

Improvement in gene translation efficiency can also be achieved by, for example, codon modification. Specifically, for example, in a case where heterologous expression of a gene is performed, and the like, translation efficiency of the gene can be improved by replacing rare codons present in the gene with synonymous codons used more frequently.

Codon substitution can be performed by, for example, a site-directed mutagenesis method in which a target mutation is introduced into a target site in a DNA. Examples of the site-directed mutagenesis method include a method using PCR [Higuchi, R., 61, in PCR technology, Erlich, H. A. Eds., Stockton press (1989); Carter, P., Meth. In Enzymol., 154, 382 (1987)], and a method using phage [Kramer, W. and Frits, H. J., Meth. In Enzymol., 154, 350 (1987); Kunkel, T. A. et al., Meth. In Enzymol., 154, 367 (1987)]. Alternatively, a gene fragment in which codons have been substituted may be totally synthesized. A frequency of codon usage in various organisms is described in "Codon usage database" [www.kazusa.or.jp/codon; Nakamura, Y. et al, Nucl. Acids Res., 28, 292 (2000)].

In addition, expression of a gene can also be increased by amplifying a regulator that increases expression of a gene, or by deleting or weakening a regulator that decreases expression of a gene. Such techniques for increasing expression of a gene as described above may be used alone or may be used in any combination.

An increase in expression of a gene can be checked, for example, by checking an increase in transcription amount of the gene or by checking an increase in an amount of a protein expressed from the gene. In addition, an increase in expression of a gene can be checked, for example, by checking an increase activity of a protein expressed from the gene.

Checking an increase in transcription amount of a gene can be performed by comparing an amount of mRNA transcribed from the gene with an unmodified strain such as a wild strain or a parent strain. Examples of methods for evaluating an amount of mRNA include Northern hybridization, RT-PCR, and the like [Sambrook, J., et al., Molecular Cloning A Laboratory Manual/Third Edition, Cold spring Harbor Laboratory Press, Cold spring Harbor (USA), 2001]. An increase in an amount of mRNA refers to, for example, the case in which an amount of mRNA has preferably increased 1.5-fold or more, has more preferably increased 2-fold or more, and has even more preferably increased 3-fold or more, as compared to that of an unmodified strain.

An increase in amount of protein can be checked by, for example, Western blot using an antibody. An increase in amount of protein refers to, for example, the case in which an amount of protein has preferably increased 1.5-fold or more, has more preferably increased 2-fold or more, and has even more preferably increased 3-fold or more, as compared to that of an unmodified strain.

An increase in an activity of a protein can be checked by, for example, measuring the activity of the protein. The increase in the activity of the protein refers to, for example, the case in which an activity of a protein has preferably increased 1.5-fold or more, has more preferably increased 2-fold or more, and has even more preferably increased 3-fold or more, as compared to that of an unmodified strain.

The above-described techniques for increasing expression of a gene can be used for enhancing expression of each of the genes (a1) and (a2) above.

Genetic modification that increases expression of the kpsS gene is preferably at least one of modification of expression control regions of the kpsS gene and genetic modification that increases the copy number. A kpsFEDUCS gene is present as a heparosan-producing gene group, but as will be described later in the Examples, the inventors of the present invention have found that an effect of particularly improving production of heparosan is obtained by increasing expression of only the kpsS gene among them. Accordingly, as the genetic modification that increases expression of the kpsS gene, a genetic modification for increasing the copy number of the kpsS gene is particularly preferable.

A genetic modification that increases expression of at least one gene selected from the kfiA, kfiB, kfiC, and kfiD genes is preferably at least one of a modification of expression control regions of at least one gene selected from the kfiA, kfiB, kfiC, and kfiD genes, and increasing the copy number of the genes. As shown in FIG. 1, the kfiA, kfiB, kfiC, and kfiD genes constitute an operon. A genetic modification that enhances the entire operon constituted by the kfiA, kfiB, kfiC, and kfiD genes is preferable, and a modification of expression control regions of the kfiA, kfiB, kfiC, and kfiD genes is more preferable.

Genetic Modification that Causes Loss of Gene Function

Examples of genetic modifications that causes loss of function of the yhbJ gene of (a3) above include a genetic modification in which a function of a protein encoded by a part corresponding to yhbJ is reduced or completely stopped by modifying a DNA encoding the part corresponding to yhbJ in a genomic DNA of a microorganism belonging to prokaryotes as a host.

In the method of the present invention, a form of modification to be added to the DNA encoding the part corresponding to yhbJ is not particularly limited as long as a function of a protein encoded by the gene corresponding to yhbJ is reduced or completely stopped, and a known method can be appropriately used.

Examples of the form that reduces or completely stops a function of a protein encoded by the part corresponding to yhbJ include any one of the following modifications (I) to (III):
  (I) All or a part of the DNA encoding the part corresponding to yhbJ is removed.
  (II) One or several substitutions, deletions, or additions are made to the DNA encoding the part corresponding to yhbJ.
  (III) The DNA encoding the part corresponding to yhbJ is replaced with a DNA sequence having less than 80% identical to a DNA sequence before modification.

Examples of loss of a function of the yhbJ gene include the case in which an activity of the yhbJ gene is preferably 20% or less, more preferably 10% or less, and even more preferably 5% or less, as compared with that of an unmodified strain. An activity of yhbJ can be checked by examining an expression level of glmS by a Northern blotting method, a Western blotting method, or the like [Kalamorz F. et al, (2007) "Feedback control of glucosamine-6-phosphate synthase GlmS expression depends on the small RNA GlmZ and involves the novel protein YhbJ in *Escherichia coli.*" Mol Microbiol. 65 (6):1518-33].

In the method for producing a sulfated polysaccharide of the present invention, it is possible to use, for a reaction solution, N-sulfoheparosan that is obtained by chemically modifying heparosan by a known method, where the heparosan being obtained by the above-described method for producing heparosan.

Method for Producing PAPS

The method for producing PAPS of the present invention is characterized in that a PAPS production reaction is carried out by incorporating an ATP source, a sulfate ion source, the above-described transformant (a) or the treated matter thereof into a reaction solution. That is, the method for producing PAPS of the present invention comprises the following steps (i) and (ii):

(i) preparing a transformant of a bacterium of the genus *Corynebacterium*, which comprises at least a gene encoding an ATP sulfurylase and a gene encoding an APS kinase which are introduced thereinto in an expressible manner, in which a cell plasma membrane of the transformant is substance-permeable, or a treated matter of the transformant; and (ii) conducting a reaction for producing PAPS by using a reaction solution containing an ATP source, a sulfate ion source, and the transformant prepared in the step (i) or the treated matter thereof.

According to the method for producing PAPS of the present invention, PAPS can be produced by a bacterial cell reaction using a transformant of bacterium of the genus *Corynebacterium* expressing the ATP sulfurylase and the APS kinase or a treated matter thereof.

EXAMPLES

Examples are shown below, but the present invention is not limited to the following examples.

Example 1

Construction of *Corynebacterium ammoniagenes* DE3 Plasmid

A plasmid for inserting lambda DE3 containing a T7 RNA polymerase gene between gltD-purT on the chromosome of a *Corynebacterium ammoniagenes* wild strain ATCC 6872 was constructed as follows. Two kinds of primers for amplifying the gltD side [gltD-purT_1 (SEQ ID NO: 1) and gltD-purT_2BX (SEQ ID NO: 2)], and two kinds of primers for amplifying the purT side [gltD-purT_3BX] (SEQ ID NO: 3) and gltD-purT_4 (SEQ ID NO: 4)] were designed.

At this time, in order to perform a second PCR (fusion PCR) for linking a gltD flanking fragment and a purT flanking fragment amplified in the first PCR, a sequence which is complementary to the sequence of about 25 bases on the 3' side of the 5' primer (gltD-purT_4; SEQ ID NO: 4) for amplifying the purT flanking fragment was added on the 5' side of the 3' primer (gltD-purT_2BX; SEQ ID NO: 2) for amplifying the gltD flanking fragment. In addition, a sequence for In-Fusion cloning was added to the 5' side of the 5' primer (gltD-purT_1) for amplifying the gltD flanking fragment and the 3' primer (gltD-purT_4) for amplifying the purT flanking fragment. Furthermore, BglII and XhoI recognition sequences were added to a liking part on the gltD side and purT side to insert lambda DE3.

A chromosomal DNA of a *Corynebacterium ammoniagenes* ATCC 6872 strain (hereinafter referred to as ATCC 6872), which is a wild-type strain of *Corynebacterium ammoniagenes*, was prepared according to the method of Saito et al. [Biochim. Biophys. Acta 72, 619 (1963)].

Using the chromosomal DNA as a template, the first PCR for amplifying the gltD flanking fragment and the purT flanking fragment was performed, and thereby about 0.8 kb of a DNA fragment on the gltD flanking and about 0.8 kb of a DNA fragment on the purT flanking were obtained. Next, the second PCR was performed to link these gltD flanking fragment and purT flanking fragment, and thereby about 1.6 kb of a DNA fragment (gltD-BX-purT) was obtained.

A plasmid pESB30, in which 2.6 kb of a PstI DNA fragment [Mol. Microbiol., 6, 1195 (1992)] containing a levansucrase gene sacB of *Bacillus subtilis* is contained at a PstI cleavage site of a vector pHSG299 of *Escherichia coli* [Gene, 61, 63, (1987)] having a kanamycin resistance gene, was cut with BamHI. Thereafter, the gltD-BX-purT fragment obtained above was linked using an In-Fusion cloning kit (Takara Bio Inc.). Using the reaction product, *Escherichia coli* DH5 alpha [manufactured by TOYOBO CO., LTD.] was transformed according to a conventional method [Molecular cloning: a laboratory manual, 3$^{rd}$ ed., 2001, Cold Spring Harbor Laboratory Press].

The obtained strain was cultured on an LB agar medium containing 20 microgram/ml of kanamycin [a medium which contains 10 g of bactotryptone (manufactured by Difco), 5 g of yeast extract (manufactured by Difco), 10 g of sodium chloride, and 16 g of Bacto agar (manufactured by Difco) in 1 L of water, and of which a pH was adjusted to pH 7.0], and a transformed strain was selected. After selecting a target clone by colony PCR, the transformed strain was inoculated into an LB medium containing 20 microgram/ml of kanamycin (a medium having the same composition as the LB agar medium except that no agar is contained), and cultured overnight, and thereby a plasmid was prepared from the obtained culture broth using a QIAprep Spin Miniprep Kit (Qiagen). Nucleotide sequence analysis confirmed that the plasmid has a structure in which about 1.6 kb of a gltD-BX-purT fragment was inserted into pESB30.

Subsequently, 4.5 kb of a lambda DE3 fragment was amplified by PCR using a chromosomal DNA extracted from *Escherichia coli* BL21 (DE3) as a template and using primers of DE3-for_Xho (SEQ ID NO: 5) and DE3-rev_Bgl (SEQ ID NO: 6). A XhoI recognition sequence was added to DE3-for_Xho, and a BglII recognition sequence was added to DE3-rev_Bgl. This fragment and the plasmid having the structure in which about 1.6 kb of the gltD-BX-purT fragment was inserted into pESB30 were digested with XhoI and BglII, and then linked with a DNA ligation kit (Takara Bio Inc.).

The *Escherichia coli* DH5 alpha was transformed in the same manner as described above, the strain thus obtained was cultured on an LB agar medium containing 20 microgram/ml of kanamycin, and a transformed strain was selected. The transformed strain was inoculated into an LB medium containing 20 microgram/ml of kanamycin and cultured overnight, and thereby a plasmid was prepared from the obtained culture broth using a QIAprep Spin Miniprep Kit (Qiagen). Nucleotide sequence analysis confirmed that the plasmid has a structure in which 4.5 kb of the lambda DE3 fragment was inserted between about 1.6 kb of gltD-purT on pESB30. This plasmid was designated as pC-DE3.

Example 2

Construction of Lambda DE3-Inserted Strain of *Corynebacterium ammoniagenes*

PC-DE3 was introduced into the ATCC 6872 strain by electroporation according to a method of Rest et al. [Appl. Microbiol. Biotech., 52, 541 (1999)], and kanamycin resistance strains were selected. When a structure of the chromosome obtained from one of the kanamycin resistance strains was examined by Southern hybridization [Molecular cloning: a laboratory manual, 3$^{rd}$ ed., 2001, Cold Spring Harbor Laboratory Press], it was confirmed that pC-DE3 was integrated into the chromosome by Campbell-type homologous recombination.

The transformed strain (single recombinant) was applied to a Suc agar medium [a medium which contains 100 g of sucrose, 7 g of meat extract, 10 g of peptone, 3 g of sodium chloride, 5 g of yeast extract (manufactured by Difco), and 15 g of Bacto agar (manufactured by Difco) in 1 L of water, and of which a pH was adjusted to pH 7.2], and cultured at 30 degrees C. for 1 day, and growing colonies were selected. The strain in which the sacB gene was present could not grow on this medium because it converts sucrose into a suicide substrate [J. Bacteriol., 174, 5462 (1991)]. On the other hand, a strain, in which the sacB gene had been deleted by a second homologous recombination between the lambda DE3-insertion type and the wild-type present near the chromosome, could grow on this medium without generating a suicide substrate. During this homologous recombination, either the wild-type structure or the strain in which the lambda DE3 fragment had been inserted between gltD-purT dropped together with sacB. At this time, in the strain in which the wild-type structure was dropped together with sacB, gene replacement to the lambda DE3-insertion type occurred.

A strain in which lambda DE3 was inserted between gltD-purT of ATCC 6872 was obtained by colony PCR using the second recombinant thus obtained with primers of DE3-for_Xho and DE3-rev_Bgl. This strain was designated as ATCC 6872 (DE3).

Example 3

Construction of Plasmid Having DNA Fragment for Expressing MET3-MET14

A Plasmid pCS299P [Appl. Microbiol. Biotech., 63, 592 (2004)] was digested with BamHI. PCR was performed with pCET_Fw2 (SEQ ID NO: 7) and pCET_Rv2 (SEQ ID NO: 8) and using pET21b as a template to obtain a DNA fragment containing lacI-PT7. These were purified by a QIAquick PCR Purification Kit (Qiagen) and linked using an In-Fusion cloning kit (Takara Bio Inc.). Using the reaction product, an *Escherichia coli* DH5 alpha (manufactured by TOYOBO CO., LTD.) was transformed according to a conventional method and cultured on an LB agar medium containing 20 microgram/ml kanamycin, and a transformed strain was selected. After selecting a target clone by colony PCR, the transformed strain was inoculated into an LB medium containing 20 microgram/ml of kanamycin and cultured overnight, and thereby a plasmid was prepared from the obtained culture broth using a QIAprep Spin Miniprep Kit (Qiagen). Nucleotide sequence analysis confirmed that the plasmid was a plasmid having a structure in which about 1.9 kb of a lacI-PT7 DNA fragment derived from pET21b was inserted into pCS299P. This plasmid was designated as pCET212.

Subsequently, a plasmid was constructed in which MET3 and MET14 derived from *Saccharomyces cerevisiae* were inserted downstream of a T7 promoter of pCET212. Two kinds of primers (MET3_1 (SEQ ID NO: 9) and MET3_2 (SEQ ID NO: 10)) for amplifying a MET3 from a chromosomal DNA of a *Saccharomyces cerevisiae* S288C strain (hereinafter referred to as S288C), and two kinds of primers (MET14_3 (SEQ ID NO: 11) and MET14_4 (SEQ ID NO: 12)) for amplifying MET14 were designed.

At that time, in order to perform the second PCR (fusion PCR) that links the MET3 fragment and the MET14 fragment amplified in the first PCR, a sequence which is complementary to the sequence of about 15 bases on the 5' side of the 5' primer (MET14_3; SEQ ID NO: 11) for amplifying MET14 was added to the 5' side of the 3' primer (MET3_2; SEQ ID NO: 10) for amplifying MET3, and a sequence which is complementary to the sequence of about 15 bases on the 5' side of MET3_3 was added to the 5' side of MET14_3. In addition, a sequence for In-Fusion cloning was added to the 5' side of the 5' primer (MET3_1) for amplifying MET3 and the 3' primer (MET14_4) for amplifying MET13. Using the chromosomal DNA of the S288C strain as a template, the first PCR for amplifying MET3 and MET14 was performed, and thereby about 1.5 kb of a DNA fragment of MET3 and about 0.6 kb of a DNA fragment in the downstream region were obtained. Next, the second PCR was performed to link these MET3 fragment and MET14 fragment, and thereby about 2.1 kb of a DNA fragment (MET3-MET14) was obtained. This DNA fragment was purified using a QIAquick PCR Purification Kit (Qiagen) and then ligated to pCET212 digested with NdeI and XhoI using an In-Fusion cloning kit (Takara Bio Inc.). Using the reaction product, an *Escherichia coli* DH5 alpha (manufactured by TOYOBO CO., LTD.) was transformed according to a conventional method. The strain thus obtained was cultured on an LB agar medium containing 20 microgram/ml of kanamycin, and a transformed strain was selected. After selecting a target clone by colony PCR, the transformed strain was inoculated into an LB medium containing 20 microgram/ml of kanamycin and cultured overnight, and thereby a plasmid was prepared from the obtained culture broth using a QIAprep Spin Miniprep Kit (Qiagen). Nucleotide sequence analysis confirmed that the plasmid has a structure in which about 2.1 kb of a MET3-MET14 fragment was inserted into pCET212. This plasmid was designated as pSC-3-13. By transforming pSC-3-13 into ATCC 6872 (DE3), a PAPS-producing ATCC 6872 (DE3)/pSC-3-13 strain of *Corynebacterium ammoniagenes* was obtained.

Example 4

Construction of Plasmid Having DNA Fragment for Expressing Chaperone Protein

PCR was performed using Gro_F (SEQ ID NO: 13) and Gro_R (SEQ ID NO: 14) and using a chromosomal DNA of an *Escherichia coli* BL21 (DE3) strain as a template, and thereby a DNA fragment containing GroES-GroEL was obtained. Next, PCR was performed using pKD46 [Datsenko, K. A., Warner, B. L., Proceedings of the National Academy of Science of the United States of America, Vol. 97. 6640-6645 (2000)] as a template, and using AraC_ParaB_F (SEQ ID NO: 15) and AraC_ParaB_R (SEQ ID NO: 16), and thereby a DNA fragment containing AraC_ParaB was obtained. PCR was performed using pCDF-SmOri-F (SEQ ID NO: 17) and pCDF-SmOri-R (SEQ ID NO: 18) and using pCDF-Duet1 (Novagen) as a template, and thereby a DNA fragment containing a streptomycin resistance gene and a ColdDF replication origin was obtained. These were purified by a QIAquick PCR Purification Kit (Qiagen) and linked using an In-Fusion cloning kit (Takara Bio Inc.). Using the reaction product, an *Escherichia coli* DH5 alpha (manufactured by TOYOBO CO., LTD.) was transformed according to a conventional method and cultured on an LB agar medium containing 50 microgram/ml of streptomycin, and a transformed strain was selected. After selecting a target clone by colony PCR, the transformed strain was inoculated into an LB medium containing 50 microgram/ml of streptomycin and cultured overnight, and thereby a plasmid was prepared from the obtained culture broth using a QIAprep Spin Miniprep Kit (Qiagen). Nucleotide sequence analysis confirmed that the plasmid has a structure in which about 1.2 kb of an AraC-ParaB DNA fragment derived from pKD46 and about 2.0 kb of a GroES-GroEL DNA fragment derived from BL21 (DE3) were inserted into pCDF-Duet1. The plasmid was designated as pGro (Sm).

Example 5

Construction of *Escherichia coli* Expressing C5-epimerase, 2OST, 6OST-3, and 3OST-1

A catalytic domain region of human C5-epimerase (E53-N609) was cloned into a pMAL-C2X vector (New England Biolabs) according to a method described in the literature [Biochemical and Biophysical Research Communications Volume 339, Issue 2, 13 Jan. 2006, pages 597-602] to construct MBP-C5. The MBP-C5 was transformed into Origami-B (DE3) (Novagen) together with pGro7 (Takara Bio Inc.), and thereby an Origami-B (DE3)/MBP-C5_pGro7 strain of *Escherichia coli* expressing C5-epimerase was constructed.

SEQ ID NO: 19 shows a nucleotide sequence of a catalytic domain (R51-N356) of 2-O-sulfotransferase isoform 1 which was derived from a Chinese hamster and was codon-optimized for expression in *Escherichia coli*. PCR was performed using the artificially synthesized sequence described above as a template and primers of SEQ ID NOS: 20 and 21. This PCR fragment was cloned into pET-His6-MBP-TEV-LIC (Addgene) by a Ligation independent cloning method [Methods Mol Biol. 2009; 498: 105-115] to construct H-MBP-2OST. H-MBP-2OST was transformed into Origami-B (DE3) (Novagen) with pGro (Sm), and thereby an Origami-B (DE3)/H-MBP-2OST_pGro (Sm) strain of *Escherichia coli* expressing 2OST was constructed.

A catalytic domain (P120-L424) of 6-O-sulfotransferase isoform 3 derived from a mouse was cloned into a pMAL-C2X vector (New England Biolabs) by a method described in the literature [Chemistry & Biology Volume 14, Issue 9, 21 Sep. 2007, pages 986-993] to construct MBP-6OST3. MBP-6OST3 was transformed into Origami-B (DE3) (Novagen) together with pGro7 (Takara Bio Inc.), and thereby an Origami-B (DE3)/MBP-6OST3_pGro7 strain of *Escherichia coli* expressing 6OST-3 was constructed.

A catalytic domain (G48-H311) of 3-O sulfotransferase derived from a mouse was cloned into a pET28a vector (Novagen) by a method described in the literature [J Biol Chem. 2004 Jun. 11; 279 (24): 25789-97] to construct HIS-3OST1. HIS-3OST1 was transformed into BL21-CodonPlus (DE3)-RIL (Agilent Technologies) together with pGro (Sm), and thereby a RIL/HIS-3OST1_pGro (Sm) strain of *Escherichia coli* expressing 3OST1 was constructed.

Example 6

Preparation of N-sulfoheparosan and 2-O-sulfated N-sulfoheparosan

Heparosan was produced by fermentation using an *Escherichia coli* K5 strain or Nissle strain according to a method described in Patent Literature [WO2018/048973 A1]. According to the literature, the obtained heparosan was chemically deacetylated and depolymerized, and then chemically N-sulfated. Thereafter, fractionation was performed by ethanol precipitation to obtain N-sulfoheparosan. The obtained N-sulfoheparosan was subjected to epimerization of C5 position and sulfation of the 2-O position in uronic acid residues by enzymatic reaction according to the same literature, and then subjected to fractionation by ethanol precipitation, and thereby 2-O-sulfated N-sulfoheparosan was obtained.

Example 7

Culture of ATCC 6872 (DE3)/pSC-3-13

The ATCC 6872 (DE3)/pSC-3-13 strain obtained in Example 3 was inoculated on a BY-Glucose agar medium containing 50 microgram/ml of kanamycin [a medium containing 10 g of glucose, 20 g of ordinary bouillon medium (manufactured by Kyokuto Pharmaceutical Industrial Co., Ltd.), 5 g of yeast extract (manufactured by Difco), and 20 g of Bacto agar (manufactured by Difco) in 1 L of water], and cultured at 30 degrees C. overnight.

Bacterial cells of two plates were inoculated into 350 ml of a primary seed medium [a medium which contains glucose 50 g/L, High Polypeptone (Nihon Pharmaceutical Co., Ltd.) 10 g/L, yeast extract (Asahi) 10 g/L, $KH_2PO_4$ 1 g/L, $K_2HPO_4$ 1 g/L, $(NH_4)_2SO_4$ 0.5 g/L, urea 0.5 g/L, L-cystine 0.03 g/L, $MgSO_4$-$7H_2O$ 1 g/L, $CaCl_2$-$2H_2O$ 0.1 g/L, $ZnSO_4$-$7H_2O$ 0.01 g/L, $FeSO_4$-$7H_2O$ 0.01 g/L, $MnSO_4$-$5H_2O$ 0.02 g/L, D-calcium pantothenate 0.01 g/L, biotin 40 microgram/L, thiamine hydrochloride 0.005 g/L, and nicotinic acid 0.005 g/L, of which a pH was adjusted to pH 7.2 with sodium hydroxide, and to which L-cysteine 0.1 g/L, sodium thiosulfate 1 g/L, and kanamycin 0.1 g/L were separately added after sterilization at 122 degrees C. for 20 minutes using an autoclave] in a 2 L Erlenmeyer flask, and cultured at 30 degrees C. at a stirring speed of 220 rpm for 24 hours.

Into 1700 ml of a secondary seed medium [a medium which contains glucose 100 g/L, fructose 4 g/L, yeast extract (manufactured by Asahi) 10 g/L, $KH_2PO_4$ 1.25 g/L, $K_2HPO_4$ 1 g/L, sodium glutamate monohydrate 2.1 g/L, L-cystine 0.02 g/L, $MgSO_4$-$7H_2O$ 1.25 g/L, $CaCl_2$-$2H_2O$ 0.1 g/L, $CuSO_4$-$5H_2O$ 0.002 g/L, $ZnSO_4$-$7H_2O$ 0.01 g/L, $FeSO_4$-$7H_2O$ 0.02 g/L, $MnSO_4$-$5H_2O$ 0.02 g/L, D-calcium pantothenate 0.015 g/L, biotin 40 microgram/L, nicotinic acid 0.005 g/L, and ADEKA NOL LG-109 (manufactured by ADEKA) 1 ml/L, of which a pH was adjusted to 7.2 with sodium hydroxide, which was sterilized in an autoclave at 122 degrees C. for 20 minutes after separately adding urea to 3.2 g/L, and to which thiamine hydrochloride 0.1 g/L, L-cysteine 0.3 g/L, sodium thiosulfate 2.5 g/L, and kanamycin 0.2 g/L were separately added] in a 6 L culture tank, 300 ml of the above culture solution was inoculated and cultured for 24 hours under culture conditions of 30 degrees C., a stirring speed of 650 rpm, and an aeration rate of 2 L/min while adjusting its pH to 6.8 with 18% aqueous ammonia.

Into 1700 ml of a main culture medium [a medium which contains $KH_2PO_4$ 10 g/L, $K_2$ $HPO_4$ 10 g/L, sodium glutamate monohydrate 1 g/L, L-cystine 0.02 g/L, $CaCl_2$-$2H_2O$ 0.1 g/L, $CuSO_4$-$5H_2O$ 0.005 g/L, $ZnSO_4$-$7H_2O$ 0.01 g/L, $FeSO_4$-$7H_2O$ 0.02 g/L, biotin 150 microgram/L, nicotinic acid 0.005 g/L, urea 2 g/L, and ADEKA NOL LG-109 (manufactured by ADEKA) 1 ml/L, and to which glucose 125 g/L, fructose 25 g/L, $MgSO_4$-$7H_2O$ 10 g/L, $MnSO_4$-$5H_2O$ 0.02 g/L, D-calcium pantothenate 0.015 g/L, thiamine hydrochloride 0.005 g/L, L-cysteine 0.15 g/L, sodium thiosulfate 2.5 g/L, and kanamycin 0.2 g/L were separately added after sterilization at 122 degrees C. for 20 minutes in an autoclave] in a 6 L culture tank, 300 ml of the above culture solution was inoculated and cultured for 25 hours under culture conditions of 30 degrees C. and an aeration rate of 2 L/min while adjusting a stirring speed between 650 rpm and 900 rpm so that an amount of oxygen dissolved does not fall below 1 ppm, and while adjusting its pH to 6.8 with 18% ammonia water.

During this period, IPTG was added so that a final concentration became 1 mM after 6 hours from the start of culture, and biotin 100 microgram/L, nicotinic acid 0.015 g/L, calcium D-pantothenate 0.015 g/L, and thiamine hydrochloride 0.005 g/L were further added after 10 hours from the start of culture. After completion of the culture, the culture solution was separated into bacterial cells and a culture supernatant by a centrifuge and thereby a pellet was obtained as wet bacterial cells and frozen at −80 degrees C.

Example 8

Culture of Origami-B (DE3)/MBP-C5_pGro7, Origami-B (DE3)/H-MBP-2OST_pGro (Sm), Origami-B (DE3)/MBP-6OST3_pGro7, and RIL/HIS-3OST1_pGro (Sm)

The Origami-B (DE3)/MBP-C5_pGro7 strain obtained in Example 5 was inoculated into a large test tube containing 5 mL of a TB medium containing 50 microgram/mL ampicillin, 20 microgram/mL chloramphenicol, 15 microgram/mL tetracycline, and 15 microgram/mL kanamycin, and was cultured at 30 degrees C. for 16 hours. The 1.2% culture solution was inoculated into a baffled Erlenmeyer flask containing 500 mL of a TB medium containing 50 microgram/mL ampicillin, 20 microgram/mL chloramphenicol, 15 microgram/mL tetracycline, and 15 microgram/mL kanamycin, and was shaking-cultured at 37 degrees C. for 6 hours. Thereafter, IPTG at a final concentration of 1 mM and arabinose at a final concentration of 4 mM were added thereto, and culture was performed at 28 degrees C. for 20 hours. Thereafter, the culture solution was centrifuged, and thereby a pellet was obtained as wet bacterial cells and frozen at −80 degrees C.

The Origami-B (DE3)/H-MBP-2OST_pGro (Sm) strain obtained in Example 5 was inoculated into a large test tube containing 5 mL of a TB medium containing 50 microgram/mL ampicillin, 50 microgram/mL streptomycin, 15 microgram/mL tetracycline, and 15 microgram/mL kanamycin, and was cultured at 30 degrees C. for 16 hours. The 1.2% culture solution was inoculated into a baffled Erlenmeyer flask containing 500 mL of a TB medium containing 50 microgram/mL ampicillin, 50 microgram/mL streptomycin, 15 microgram/mL tetracycline, and 15 microgram/mL kanamycin, and was shaking-cultured at 30 degrees C. for 12 hours. Thereafter, IPTG at a final concentration of 1 mM and arabinose at a final concentration of 4 mM were added thereto, and culture was performed at 28 degrees C. for 20 hours. Thereafter, the culture solution was centrifuged, and thereby a pellet was obtained as wet bacterial cells and frozen at −80 degrees C.

The Origami-B (DE3)/MBP-6OST3_pGro7 strain obtained in Example 5 was inoculated into a large test tube containing 5 mL of a TB medium containing 50 microgram/mL ampicillin, 20 microgram/mL chloramphenicol, 15 microgram/mL tetracycline, and 15 microgram/mL kanamycin, and was cultured at 30 degrees C. for 16 hours. The 1.2% culture solution was inoculated into a baffled Erlenmeyer flask containing 500 mL of a TB medium containing 50 microgram/mL ampicillin, 20 microgram/mL chloramphenicol, 15 microgram/mL tetracycline, and 15 microgram/mL kanamycin, and was shaking-cultured at 37 degrees C. for 4 hours. Thereafter, IPTG at a final concentration of 1 mM and arabinose at a final concentration of 4 mM were added thereto, and culture was performed at 28 degrees C. for 20 hours. Thereafter, the culture solution was centrifuged, and thereby a pellet was obtained as wet bacterial cells and frozen at −80 degrees C.

The RIL/HIS-3OST1_pGro (Sm) strain obtained in Example 5 was inoculated into a large test tube containing 5 mL of a TB medium containing 50 microgram/mL of streptomycin, 15 microgram/mL of kanamycin, and was cultured at 30 degrees C. for 16 hours. The 1.2% culture solution was inoculated into a baffled Erlenmeyer flask containing 500 mL of a TB medium containing 50 microgram/mL streptomycin and 15 microgram/mL kanamycin, and was shaking-cultured at 37 degrees C. for 4 hours. Thereafter, IPTG at a final concentration of 1 mM and arabinose at a final concentration of 4 mM were added thereto, and culture was performed at 28 degrees C. for 20 hours. Thereafter, the culture solution was centrifuged, and thereby a pellet was obtained as wet bacterial cells and frozen at −80 degrees C.

Example 9

Test for Sulfation Reaction at 2-O Position of N-Sulfoheparosan Using ATCC 6872 (DE3)/pSC-3-13, Origami-B (DE3)/MBP-C5_pGro7 and Origami-B (DE3)/H-MBP-2OST_pGro (Sm)

Each of the frozen bacterial cells of ATCC 6872 (DE3)/pSC-3-13, Origami-B (DE3)/MBP-C5_pGro7, and Origami-B (DE3)/H-MBP-2OST_pGro (Sm) obtained in Examples 7 and 8 was suspended in distilled water so that a weight of the frozen bacterial cells became 333 g/L to prepare a bacterial cell suspension. Thus obtained 30 ml of the ATCC 6872 (DE3)/pSC-3-13 bacterial cell suspension, 6 ml of Origami-B (DE3)/MBP-C5_pGro7 bacterial cell suspension, and 6 mL of Origami-B (DE3)/H-MBP-2OST_pGro (Sm) bacterial cell suspension were added to 18 ml of the reaction solution [an aqueous solution containing glucose 60 g/L, $KH_2PO_4$ 8.75 g/L, $K_2HPO_4$ 15 g/L, $MgSO_4\cdot7H_2O$ 20 g/L, D-calcium pantothenate 0.3 g/L, nicotinic acid 0.2 g/L, adenine 4.05 g/L, benzalkonium chloride 1.25 g/L, ADEKA NOL LG-109 (manufactured by ADEKA) 1 ml/L, and N-sulfoheparosan 1 g/L (produced in Example 6)] in a 250 ml bioreactor, and reacted for 22 hours under culture conditions of 37 degrees C., a stirring speed of 500 rpm, and an aeration rate of 0.75 mL/min while adjusting its pH to 6.5 with a 2.8% aqueous ammonia solution. During this period, glucose 60 g/L, $MgSO_4\cdot7H_2O$ 5.0 g/L, and adenine 2.7 g/L were further added 6 hours after the start of the reaction.

Sampling was appropriately performed during the reaction to obtain a reaction solution. The obtained reaction solution was appropriately diluted and then centrifuged, and PAPS was detected and quantified by measuring an absorbance at 254 nm with a UV detector using HPLC manufactured by Shimadzu Corporation. The results are shown in FIG. 4. In addition, generation of unsaturated disaccharide by enzymatic digestion and analysis by HPLC were performed according to Patent Literature [WO2018/048973 A1].

That is, the obtained reaction solution was centrifuged, and the resulting supernatant was heated and maintained at 80 degrees C. for 10 minutes to denature the protein. The solution after protein denaturation was centrifuged, and the resulting supernatant was desalted by ultrafiltration using a 3 k molecular weight filter device (manufactured by Merck). The solution after desalting was supplied to a heparinase reaction solution [composed of 50 mM ammonium acetate and 2 mM calcium chloride] containing 0.5 U/ml of each of heparinases I, II, and III (manufactured by Sigma, but other heparinases can also be used), and subjected to enzymatic digestion at 35 degrees C. for 2 hours. Heparinase was inactivated by maintaining the solution after enzymatic digestion at 95 degrees C. for 15 minutes.

Unsaturated disaccharide analysis was performed by subjecting the solution after heparinase inactivation to gradient elution mode analysis of a mobile phase A [an aqueous solution which contains 1.8 mM sodium dihydrogen phosphate and of which a pH was adjusted to pH 3.0 with phosphoric acid] and a mobile phase B [an aqueous solution which contains 1.8 mM sodium dihydrogen phosphate and 1 M sodium perchlorate, and of which a pH was adjusted to pH 3.0 with phosphoric acid] using Shimadzu HPLC and strong anion exchange column (spherisorb-SAX chromatography column, 4.0×250 mm, 5 micrometer, manufactured by Waters).

Unsaturated disaccharide was detected by measuring an absorbance at 232 nm with a UV detector. A retention time of delta-UA-GlcNS and delta-UA, 2S-GlcNS was checked by comparison with an unsaturated disaccharide standard reagent (manufactured by Iduron). 2-O-sulfation was checked by obtaining an area ratio of delta-UA, 2S-GlcNS with respect to a total area of the detected delta-UA-GlcNS and delta-UA, 2S-GlcNS. The results are shown in FIG. 5.

Example 10

Test for Sulfation Reaction at 6-O Position of 2-O-Sulfated N-Sulfoheparosan Using ATCC 6872 (DE3)/pSC-3-13 and Origami-B (DE3)/MBP-6OST3_pGro7

Each of the frozen bacterial cells of ATCC 6872 (DE3)/pSC-3-13 and Origami-B (DE3)/MBP-6OST3_pGro7 obtained in Examples 7 and 8 was suspended in distilled water so that a weight of the frozen bacterial cells became 333 g/L to prepare a bacterial cell suspension. Thus obtained 30 ml of the ATCC 6872 (DE3)/pSC-3-13 bacterial cell suspension and 6 ml of Origami-B (DE3)/MBP-6OST3_pGro7 bacterial cell suspension as well as 6 ml of distilled water were added to 18 ml of the reaction solution [an aqueous solution containing glucose 60 g/L, $KH_2PO_4$ 8.75 g/L, $K_2HPO_4$ 15 g/L, $MgSO_4$-$7H_2O$ 20 g/L, D-calcium pantothenate 0.3 g/L, nicotinic acid 0.2 g/L, adenine 4.05 g/L, benzalkonium chloride 1.25 g/L, ADEKA NOL LG-109 (manufactured by ADEKA) 1 ml/L, and 2-O-sulfated N-sulfoheparosan 0.5 g/L (produced in Example 6)] in a 250 ml bioreactor, and reacted for 22 hours under culture conditions of 32 degrees C., a stirring speed of 500 rpm, and an aeration rate of 0.75 mL/min while adjusting its pH to 7.4 with an aqueous solution of 2N potassium hydroxide.

During this period, glucose 60 g/L, $MgSO_4$-$7H_2O$ 5.0 g/L, and adenine 2.7 g/L were further added 6 hours after the start of the reaction. Sampling was appropriately performed during the reaction to obtain a reaction solution. Using the same method as in Example 9, detection and quantification of PAPS were performed. The results are shown in FIG. 6.

In addition, the sulfated composition contained in the sugar chain after the reaction was analyzed by the same method as in Example 9. A retention time of delta-UA, 2S-GlcNS and delta-UA, 2S-GlcN, 6S was checked by comparison with an unsaturated disaccharide standard reagent (manufactured by Iduron). 6-O-sulfation was checked by obtaining an area ratio of delta-UA, 2S-GlcN, 6S with respect to a total area of the detected delta-UA, 2S-GlcNS and delta-UA, 2S-GlcN, 6S. The results are shown in FIG. 7.

Example 11

Test for Sulfation Reaction at 6-O Position and 3-O Position of 2-O-Sulfated N-Sulfoheparosan Using ATCC 6872 (DE3)/pSC-3-13, Origami-B (DE3)/MBP-6OST3_pGro7, and RIL/HIS-3OST1_pGro (Sm)

The reaction was carried out for 22 hours under the conditions described in Example 10. During this period, 3 hours after the start of the reaction, the frozen bacterial cells of IL/HIS-3OST1_pGro (Sm) obtained in Example 8 were suspended in distilled water so that a weight of the frozen bacterial cells became 333 g/L, and 6 ml of the prepared bacterial cell suspension was added. Sampling was appropriately performed during the reaction to obtain a reaction solution. Using the same method as in Example 9, detection and quantification of PAPS were performed. The results are shown in FIG. 8.

After completion of the reaction, the reaction solution was centrifuged, the resulting supernatant was appropriately diluted, and thereafter, an anti-IIa activity was measured using a BIOPHEN (trademark) ANTI-IIa measurement kit (manufactured by Hyphen Biomed) to check 3-O-sulfation. In addition, the anti-IIa activity of the solution after the reaction of Example 10 was also measured as a negative control to which RIL/HIS-3OST1_pGro (Sm) was not added. A calibration curve was created using a BIOPHEN (trademark) UFH Calibrator (manufactured by Hyphen Biomed). The results are shown in Table 1.

TABLE 1

| Measurement results of anti-IIa activity | |
| --- | --- |
| Addition of RIL/HIS-3OST1_pGro (Sm) | Anti-IIa activity (IU/ml - supernatant) |
| Added | 375 |
| Not added | −36 |

Example 12

The frozen bacterial cells of ATCC 6872 (DE3)/pSC-3-13 obtained in Examples 7 was suspended in distilled water so that a weight of the frozen bacterial cells became 333 g/L to prepare a bacterial cell suspension. Thus obtained 30 ml of the bacterial cell suspension was added to 30 ml of the reaction solution [an aqueous solution containing glucose 60 g/L, $KH_2PO_4$ 8.75 g/L, $K_2HPO_4$ 15 g/L, $MgSO_4$-$7H_2O$ 20 g/L, D-calcium pantothenate 0.3 g/L, nicotinic acid 0.2 g/L, adenine 4.05 g/L, benzalkonium chloride 0.625 g/L, ADEKA NOL LG-109 (manufactured by ADEKA) 1 ml/L] in a 250 ml bioreactor, and reacted for 22 hours under culture conditions of 32 degrees C., a stirring speed of 500 rpm, and an aeration rate of 0.75 mL/min while adjusting its pH to 7.4 with an aqueous solution of 2N potassium hydroxide.

During this period, glucose 60 g/L, $KH_2PO_4$ 2.19 g/L, $K_2HPO_4$ 3.75 g/L, $MgSO_4$-$7H_2$ O 5.0 g/L, and adenine 2.7 g/L were further added 6 hours after the start of the reaction. Sampling was appropriately performed during the reaction to obtain a reaction solution.

The obtained reaction solution was appropriately diluted and then centrifuged, and PAPS was detected and quantified by measuring an absorbance at 254 nm with a UV detector using HPLC manufactured by Shimadzu Corporation. The results are shown in FIG. 9.

As described above, a bacterium of the genus *Corynebacterium* capable of producing and regenerating PAPS, and a microorganism belonging to prokaryotes expressing a sulfation enzyme were added to and reacted with raw materials such as glucose, adenine, and magnesium sulfate, and thereby sulfated polysaccharides were efficiently produced from polysaccharides.

While the invention has been described in detail and with reference to specific embodiments thereof, it will be apparent to one skill in the art that various changes and modifications can be made therein without departing from the spirit and scope thereof. All references cited herein are incorporated in their entirety. This application is based on International application No. PCT/JP2020/015388 filed on Apr. 3, 2020, the entire contents of which are incorporated hereinto by reference.

The invention claimed is:

1. A method for producing a sulfated polysaccharide, the method comprising the following steps (1-1) and (1-2):

(1-1) preparing a transformant (a) of a bacterium of the genus *Corynebacterium*, comprising at least a gene encoding an adenosine 5'-triphosphate (ATP) sulfurylase and a gene encoding an adenosine 5'-phosphosulfate (APS) kinase which are introduced thereinto in an expressible manner and in which gene expression of an enzyme related to degradation of 3'-phosphoadenosine 5'-phosphosulfate (PAPS) is not attenuated, or a treated matter of the transformant (a), wherein the treated matter of transformant (a) is a matter in which the cell plasma membrane of the transformant (a) is substance permeable, and wherein the transformant (a) or the treated matter thereof is capable of producing PAPS; and (1-2) conducting a reaction for producing PAPS by using a reaction solution containing ATP or an ATP source, a sulfate ion source, and the transformant (a) or the treated matter of transformant (a), wherein the enzyme related to degradation of PAPS is not heat inactivated; and wherein the method further comprises conducting sulfation by a transformant comprising a gene encoding sulfotransferase, which is introduced thereinto in an expressible manner, or a treated matter or extract of the transformant comprising a gene encoding sulfotransferase.

2. The method for producing a sulfated polysaccharide according to claim 1, the method further comprising the following steps (2-1) and (2-2):
  (2-1) preparing a transformant (b) of a microorganism belonging to prokaryotes, comprising at least a gene encoding a C5-epimerase which is introduced thereinto in an expressible manner, or a treated matter of transformant (b), or an extract of the transformant (b), wherein the treated matter of transformant (b) is a matter in which the cell plasma membrane of the transformant (b) is substance permeable, wherein the extract of the transformant (b) is a crude enzyme extract, a purified enzyme, a concentrate of a culture, or a dried product of a culture, and wherein the transformant (b), the treated matter of transformant (b), or the extract of transformant (b) is capable of effecting C5-epimerization; and
  (2-2) conducting C5-epimerization by incorporating the transformant (b), the treated matter of transformant (b), or the extract of transformant (b) in the reaction solution in the presence of N-sulfoheparosan.

3. The method for producing a sulfated polysaccharide according to claim 1, wherein the sulfotransferase comprises a 2-O-sulfotransferase.

4. The method for producing a sulfated polysaccharide according to claim 1, the method further comprising the following steps (3'-1) to (3'-2):
  (3'-1) preparing a transformant (b) of a microorganism belonging to prokaryotes, comprising at least a gene encoding a C5-epimerase which is introduced thereinto in an expressible manner, or a treated matter of transformant (b), or an extract of the transformant (b), wherein the treated matter of transformant (b) is a matter in which the cell plasma membrane of the transformant (b) is substance permeable, wherein the extract of the transformant (b) is a crude enzyme extract, a purified enzyme, a concentrate of a culture, or a dried product of a culture, and wherein the transformant (b), the treated matter of transformant (b), or the extract of transformant (b) is capable of effecting C5-epimerization; and
  (3'-2) conducting C5-epimerization by incorporating the transformant (b), the treated matter of transformant (b), or the extract of transformant (b) in the reaction solution in the presence of N-sulfoheparosan, wherein the sulfotransferase comprises a 2-O-sulfotransferase.

5. The method for producing a sulfated polysaccharide according to claim 3, wherein the sulfotransferase comprises a 6-O-sulfotransferase.

6. The method for producing a sulfated polysaccharide according to claim 3, wherein the sulfotransferase comprises a 3-O-sulfotransferase.

7. The method for producing a sulfated polysaccharide according to claim 1, which is for producing heparin.

8. A method for producing 3'-phosphoadenosine 5'-phosphosulfate (PAPS), the method comprising the following steps (i) and (ii):
  (i) preparing a transformant of a bacterium of the genus *Corynebacterium*, comprising at least a gene encoding an adenosine 5'-triphosphate (ATP) sulfurylase and a gene encoding an adenosine 5'-phosphosulfate (APS) kinase which are introduced thereinto in an expressible manner and in which gene expression of an enzyme related to degradation of PAPS is not attenuated, or a treated matter of the transformant, wherein the treated matter is a matter in which the cell plasma membrane of the transformant is substance permeable, and wherein the transformant or the treated matter of the transformant is capable of producing PAPS; and
  (ii) conducting a reaction for producing PAPS by using a reaction solution containing ATP or an ATP source, a sulfate ion source, and the transformant prepared in the step (i) or the treated matter thereof, wherein the enzyme related to degradation of PAPS is not heat inactivated.

9. The method for producing a sulfated polysaccharide according to claim 4, wherein the sulfotransferase comprises a 6-O-sulfotransferase.

10. The method for producing a sulfated polysaccharide according to claim 4, wherein the sulfotransferase comprises a 3-O-sulfotransferase.

* * * * *

```
                            SEQUENCE LISTING

<160> NUMBER OF SEQ ID NOS: 32

<210> SEQ ID NO 1
<211> LENGTH: 35
<212> TYPE: DNA
<213> ORGANISM: Artificial Sequence
<220> FEATURE:
<223> OTHER INFORMATION: Synthesized Oligonucleotide for primer

<400> SEQUENCE: 1
cggtacccgg ggatccgact ggccagtaca ggctg                              35

<210> SEQ ID NO 2
<211> LENGTH: 40
<212> TYPE: DNA
<213> ORGANISM: Artificial Sequence
<220> FEATURE:
<223> OTHER INFORMATION: Synthesized Oligonucleotide for primer

<400> SEQUENCE: 2
agcgactcga gtttagatct tcaatgctca acccgacctg                         40

<210> SEQ ID NO 3
<211> LENGTH: 40
<212> TYPE: DNA
<213> ORGANISM: Artificial Sequence
<220> FEATURE:
<223> OTHER INFORMATION: Synthesized Oligonucleotide for primer

<400> SEQUENCE: 3
attgaagatc taaactcgag tcgcttgacg atgttcaact                         40

<210> SEQ ID NO 4
<211> LENGTH: 35
<212> TYPE: DNA
<213> ORGANISM: Artificial Sequence
<220> FEATURE:
<223> OTHER INFORMATION: Synthesized Oligonucleotide for primer

<400> SEQUENCE: 4
cgactctaga ggatcgtttg tcgcgggcga cgata                              35

<210> SEQ ID NO 5
<211> LENGTH: 30
<212> TYPE: DNA
<213> ORGANISM: Artificial Sequence
<220> FEATURE:
<223> OTHER INFORMATION: Synthesized Oligonucleotide for primer

<400> SEQUENCE: 5
tttctcgaga actgcgcaac tcgtgaaagg                                    30
```

```
<210> SEQ ID NO 6
<211> LENGTH: 28
<212> TYPE: DNA
<213> ORGANISM: Artificial Sequence
<220> FEATURE:
<223> OTHER INFORMATION: Synthesized Oligonucleotide for primer

<400> SEQUENCE: 6
tttagatctg ttacgcgaac gcgaagtc                                      28

<210> SEQ ID NO 7
<211> LENGTH: 36
<212> TYPE: DNA
<213> ORGANISM: Artificial Sequence
<220> FEATURE:
<223> OTHER INFORMATION: Synthesized Oligonucleotide for primer

<400> SEQUENCE: 7
cggtacccgg ggatcgctta atgcgccgct acaggg                             36

<210> SEQ ID NO 8
<211> LENGTH: 35
<212> TYPE: DNA
<213> ORGANISM: Artificial Sequence
<220> FEATURE:
<223> OTHER INFORMATION: Synthesized Oligonucleotide for primer

<400> SEQUENCE: 8
atgcctgcag gtcgaggagc tgactgggtt gaagg                              35

<210> SEQ ID NO 9
<211> LENGTH: 35
<212> TYPE: DNA
<213> ORGANISM: Artificial Sequence
<220> FEATURE:
<223> OTHER INFORMATION: Synthesized Oligonucleotide for primer

<400> SEQUENCE: 9
gaaggagata tacatatgcc tgctcctcac ggtgg                              35

<210> SEQ ID NO 10
<211> LENGTH: 35
<212> TYPE: DNA
<213> ORGANISM: Artificial Sequence
<220> FEATURE:
<223> OTHER INFORMATION: Synthesized Oligonucleotide for primer

<400> SEQUENCE: 10
gttgtgtctc ctctattaaa atacaaaaaa gccat                              35

<210> SEQ ID NO 11
<211> LENGTH: 35
<212> TYPE: DNA
<213> ORGANISM: Artificial Sequence
<220> FEATURE:
<223> OTHER INFORMATION: Synthesized Oligonucleotide for primer

<400> SEQUENCE: 11
tagaggagac acaacatggc tactaatatt acttg                              35

<210> SEQ ID NO 12
<211> LENGTH: 35
<212> TYPE: DNA
<213> ORGANISM: Artificial Sequence
<220> FEATURE:
<223> OTHER INFORMATION: Synthesized Oligonucleotide for primer
```

<400> SEQUENCE: 12
ggtggtggtg ctcgattaca aatgcttacg gatga                                    35

<210> SEQ ID NO 13
<211> LENGTH: 61
<212> TYPE: DNA
<213> ORGANISM: Artificial Sequence
<220> FEATURE:
<223> OTHER INFORMATION: Synthesized Oligonucleotide for primer

<400> SEQUENCE: 13
ttgggaattc gagctctaag gaggttataa aaatgaata ttcgtccatt gcatgatcgc         60
g                                                                         61

<210> SEQ ID NO 14
<211> LENGTH: 24
<212> TYPE: DNA
<213> ORGANISM: Artificial Sequence
<220> FEATURE:
<223> OTHER INFORMATION: Synthesized Oligonucleotide for primer

<400> SEQUENCE: 14
ttacatcatg ccgcccatgc cacc                                                24

<210> SEQ ID NO 15
<211> LENGTH: 30
<212> TYPE: DNA
<213> ORGANISM: Artificial Sequence
<220> FEATURE:
<223> OTHER INFORMATION: Synthesized Oligonucleotide for primer

<400> SEQUENCE: 15
ttatgacaac ttgacggcta catcattcac                                          30

<210> SEQ ID NO 16
<211> LENGTH: 61
<212> TYPE: DNA
<213> ORGANISM: Artificial Sequence
<220> FEATURE:
<223> OTHER INFORMATION: Synthesized Oligonucleotide for primer

<400> SEQUENCE: 16
cgcgatcatg caatggacga atattcattt tttataacct ccttagagct cgaattccca         60
a                                                                         61

<210> SEQ ID NO 17
<211> LENGTH: 42
<212> TYPE: DNA
<213> ORGANISM: Artificial Sequence
<220> FEATURE:
<223> OTHER INFORMATION: Synthesized Oligonucleotide for primer

<400> SEQUENCE: 17
ggcggcatga tgtaattatt tgccgactac cttggtgatc tc                            42

<210> SEQ ID NO 18
<211> LENGTH: 45
<212> TYPE: DNA
<213> ORGANISM: Artificial Sequence
<220> FEATURE:
<223> OTHER INFORMATION: Synthesized Oligonucleotide for primer

<400> SEQUENCE: 18
gtcaagttgt cataatctag agcggttcag tagaaaagat caaag                         45

<210> SEQ ID NO 19
<211> LENGTH: 918
<212> TYPE: DNA
<213> ORGANISM: Chinese hamster

<400> SEQUENCE: 19

| | | | | | |
|---|---|---|---|---|---|
| cgcgaaatcg | aacagcgtca | cacgatggat | ggcccgcgcc | aagatgcaac | cctggacgaa | 60 |
| gaagaagata | tggttatcat | ctacaaccgc | gtcccgaaaa | ccgcttcaac | gtcgtttacc | 120 |
| aatattgcgt | acgacctgtg | cgccaaaaac | aaatatcatg | tgctgcacat | caataccacg | 180 |
| aaaaacaatc | cggttatgag | cctgcaggat | caagtccgtt | ttgtgaaaaa | catcacctct | 240 |
| tggaaagaaa | tgaaaccggg | cttctaccat | ggtcacgtta | gttatctgga | ctttgccaaa | 300 |
| ttcggcgtga | agaaaaaacc | gatctacatc | aacgttatcc | gtgatccgat | cgaacgcctg | 360 |
| gtctcttatt | actattttct | gcgtttcggc | gatgactatc | gcccgggtct | gcgtcgccgt | 420 |
| aaacagggtg | acaagaaaac | ctttgatgaa | tgcgtcgcag | aaggcggttc | agattgtgct | 480 |
| ccggaaaaac | tgtggctgca | gatcccgttt | ttctgcggcc | atagctctga | atgttggaac | 540 |
| gtgggttcgc | gctgggcaat | ggaccaagct | aaatacaacc | tgatcaacga | atattttctg | 600 |
| gtgggtgtta | ccgaagaact | ggaagatttc | atcatgctgc | tggaagccgc | actgccgcgc | 660 |
| tttttccgtg | gcgcgacgga | actgtaccgt | accggcaaaa | aatctcatct | gcgcaaaacc | 720 |
| acggagaaaa | aactgccgac | gaaacagacc | attgcgaaac | tgcagcaatc | cgacatctgg | 780 |
| aaaatggaaa | acgaattcta | cgaattcgcc | ctgaacagt | ttcaattcat | tcgtgcgcac | 840 |
| gccgttcgcg | aaaaagatgg | tgacctgtat | atcctggcac | aaaacttctt | ctatgaaaaa | 900 |
| atctatccga | atcaaat | | | | | 918 |

<210> SEQ ID NO 20
<211> LENGTH: 35
<212> TYPE: DNA
<213> ORGANISM: Artificial Sequence
<220> FEATURE:
<223> OTHER INFORMATION: Synthesized Oligonucleotide for primer

<400> SEQUENCE: 20
tacttccaat ccaatcgcga atcgaacag cgtca                         35

<210> SEQ ID NO 21
<211> LENGTH: 35
<212> TYPE: DNA
<213> ORGANISM: Artificial Sequence
<220> FEATURE:
<223> OTHER INFORMATION: Synthesized Oligonucleotide for primer

<400> SEQUENCE: 21
ttatccactt ccaatatttg atttcggata gattt                        35

<210> SEQ ID NO 22
<211> LENGTH: 1536
<212> TYPE: DNA
<213> ORGANISM: Saccharomyces cerevisiae

<400> SEQUENCE: 22

| | | | | | |
|---|---|---|---|---|---|
| atgcctgctc | tcacggtgg | tattctacaa | gacttgattg | ctagagatgc | gttaaagaag | 60 |
| aatgaattgt | atctgaagc | gcaatcttcg | gacattttag | tatggaactt | gactcctaga | 120 |
| caactatgtg | atattgaatt | gattctaaat | ggtgggtttt | ctcctctgac | tgggttttg | 180 |

```
aacgaaaacg attactcctc tgttgttaca gattcgagat tagcagacgg cacattgtgg    240
accatcccta ttacattaga tgttgatgaa gcatttgcta accaaattaa accagacaca    300
agaattgccc ttttccaaga tgatgaaatt cctattgcta tacttactgt ccaggatgtt    360
tacaagccaa acaaaactat cgaagccgaa aaagtcttca gaggtgaccc agaacatcca    420
gccattagct atttatttaa cgttgccggt gattattacg tcggcggttc tttagaagcg    480
attcaattac ctcaacatta tgactatcca ggtttgcgta agacacctgc caactaaga    540 cttgaattcc aatcaagaca atgggaccgt gtcgtagctt ccaaactcg taatccaatg    600 catagagccc acagggagtt gactgtgaga gccgccagag aagctaatgc taaggtgctg    660
atccatccag ttgttggact aaccaaacca ggtgatatag accatcacac tcgtgttcgt    720
gtctaccagg aaattattaa gcgttatcct aatggtattg cttctcttatc cctgttgcca    780 ttagcaatga gaatgagtgg tgatagagaa gccgtatggc atgctattat tagaaagaat    840
tatggtgcct cccacttcat tgttggtaga gaccatgcgg gcccaggtaa gaactccaag    900
ggtgttgatt tctacggtcc atacgatgct caagaattgg tcgaatccta caagcatgaa    960
ctggacattg aagttgttcc attcagaatg tcacttatt tgccagacga agaccgttat    1020
gctccaattg atcaaattga caccacaaag acgagaacct tgaacatttc aggtacagag    1080
ttgagacgcc gtttaagagt tggtggtgag attcctgaat ggttctcata tcctgaagtg    1140
gttaaaatcc taagagaatc caacccacca agaccaaaac aaggttttc aattgtttta    1200 ggtaattcat taaccgtttc tcgtgagcaa ttatccattg ctttgttgtc aacattcttg    1260
caattcggtg gtggcaggta ttacaagatc tttgaacaca ataataagac agagttacta    1320
tctttgattc aagatttcat tggttctggt agtggactaa ttattccaaa tcaatgggaa    1380
gatgacaagg actctgttgt tggcaagcaa aacgtttact tattagatac ctcaagctca    1440
gccgatattc agctagagtc agcggatgaa cctatttcac atattgtaca aaaagttgtc    1500
ctattcttgg aagacaatgg ctttttttgta ttttaa                            1536

<210> SEQ ID NO 23
<211> LENGTH: 609
<212> TYPE: DNA
<213> ORGANISM: Saccharomyces cerevisiae

<400> SEQUENCE: 23
atggctacta atattacttg gcatccaaat cttacttacg acgaacgcaa ggcattgaga     60
aaacaggacg ttgtactat ttggttaaca ggtctaagtg cgtcaggtaa aagtacaatc    120
gcctgtgcgc tagaacagtt actgctccaa aaaaacttgt ctgcatatag attggatggt    180
gacaacattc gttttggatt gaacaaggat ttgggtttct cagaaaagga cagaaatgaa    240
aacattcgta gaattagcga agtttctaag ctatttgctg attcatgtgc tatttcaatc    300
acctcattta tctctccata cagagttgac agagatagag ctcgtgaact acataaggag    360
gctggtttga agttcattga aatatttgtt gatgttccat agaagtcgc tgagcaaagg    420 gacccctaagg gtttatacaa gaaagctagg gagggtgtaa tcaaggagtt tacaggtatt    480
tctgccccat atgaagcgcc aaaagctcca gagctacatt tgagaaccga ccagaagacg    540
gttgaagaat gtgctaccat tatttatgag tacttaatca gtgaaaaaat catccgtaag    600
catttgtaa                                                           609

<210> SEQ ID NO 24
<211> LENGTH: 1695
```

<212> TYPE: DNA
<213> ORGANISM: Homo sapiens

<400> SEQUENCE: 24

```
gaaaaaagag cagcagcatc tgagagtaac aactatatga accacgtggc caaacaacag      60
tctgaggaag cattccctca ggaacagcag aaagcacccc ctgttgttgg gggcttcaat     120
agcaatgtgg gaagtaaggt gttagggctc aaatatgaag aaattgactg tctcataaat     180
gatgaacaca caattaaagg gagacgagag gggaacgaag tctttcttcc attcacttgg     240
gttgagaaat attttgatgt ttatggaaag gtggttcagt atgatggcta tgatcggttt     300
gaattctctc atagctattc caaagtctat gcacagagag cccctatca ccccgatggt      360
gtgtttatgt cttttgaagg ctacaatgtg aagtccgag acagagtcaa gtgcataagt       420
ggggttgaag gtgtgccatt atctacacaa tggggacctc aaggctattt ctatccaatc     480
cagattgcac agtatggatt aagtcattac agcaagaatc taactgagaa acctcctcac     540
atagaggtat atgaaacagc agaagacaga gacaaaaaca gcctaatga ctggactgtg       600
ccaaagggct gctttatggc gaatgtggct gataagtcta gattcaccaa tgtcaaacag     660
tttattgcac cagaaaccag tgaaggtgta tccttgcaac tgggaaacac aaaagatttt     720
attatttcat ttgacctcaa gttcttgaca aatggaagtg tgtccgtggt tctagagacc     780
acagaaaaga atcagctctt cactatacat tatgtctcaa atgctcagct aattgctttt     840
aaagaaagag atatatacta tggcattggg cccagaactt catggagcac agttaccagg     900
gacctggtca ctgaccctcag gaaggagtg ggtctttcaa acacaaaagc tgtcaagcca      960
accaaaataa tgcccaagaa ggtggttagg ttgattgcaa aaggtaaggg attcctcgac    1020
aacattacca tctctaccac agcccacatg gctgcatttt ttgctgctag tgattggcta    1080
gtaaggaacc aggatgagaa aggtggctgg ccaattatgt gacccgtaa gttaggggaa      1140
gggttcaagt ctttagagcc aggatggtat tctgccatgg cccaagggca agccatttct    1200
acattagtca gggcctatct gttaacaaaa gaccatatat tcctcaattc agctttaagg    1260
gcaacagccc cttataagtt tctatctgag cagcatggag ttaaagctgt gtttatgaat    1320
aaacatgact ggtatgaaga atatccaacc acacctagct cttttgtttt aaatggcttt    1380
atgtattctt taattgggct gtatgactta aaagaaactg caggggaaaa actcggaaaa    1440
gaagcaaggt ccttgtatga gcgtggcatg gaatctctta agccatgct gcccttgtat     1500
gacactggct caggaaccat ctatgacctc cgtcacttca tgcttggcat cgctcctaac    1560
ctggctcgct gggactatca taccacccac atcaatcagt tgcagctact cagtaccatt    1620
gatgagtccc caatcttcaa agaatttgtc aagaggtgga aaagctacct taaaggcagc    1680
agggcaaagc acaac                                                     1695
```

<210> SEQ ID NO 25
<211> LENGTH: 1695
<212> TYPE: DNA
<213> ORGANISM: Mus musculus

<400> SEQUENCE: 25

```
gaaaaaagag cagcagcatc tgagagtaac aactatatga accacgtggc caaacaacag      60
tctgaggaag cattccctca ggaacagcag aaagcacccc ctgttgttgg gggcttcaat     120
agcaatgtgg gaagtaaggt gttagggctc aaatatgaag aaattgactg tctcataaat     180
gatgaacaca caattaaagg gagacgagag gggaacgaag tctttcttcc attcacttgg     240
```

```
gttgagaaat attttgatgt ttatggaaag gtggttcagt atgatggcta tgatcggttt      300
gaattctctc atagctattc caaagtctat gcacagagag cccctatca ccccgatggt       360 gtgtttatgt cttttgaagg ctacaatgtg gaagtccgag acagagtcaa gtgcataagt     420
ggggttgaag gtgtgccatt atctacacaa tggggacctc aaggctattt ctatccaatc     480
cagattgcac agtatggatt aagtcattac agcaagaatc taactgagaa acctcctcac     540
atagaggtat atgaaacagc agaagacaga gacaaaaaca agcctaatga ctggactgtg     600
ccaaagggct gctttatggc gaatgtggct gataagtcta gattcaccaa tgtcaaacag     660
tttattgcac cagaaaccag tgaaggtgta tccttgcaac tgggaaacac aaaagatttt     720
attatttcat ttgacctcaa gttcttgaca aatggaagtg tgtccgtggt tctagagacc     780
acagaaaaga atcagctctt cactatacat tatgtctcaa atgctcagct aattgctttt     840
aaagaaagag atatatacta tggcattggg cccagaactt catggagcac agttaccagg     900
gacctggtca ctgaccctcag gaaggagtg ggtcttcaa acacaaaagc tgtcaagcca      960
accaaaataa tgcccaagaa ggtggttagg ttgattgcaa aaggtaaggg attcctcgac    1020
aacattacca tctctaccac agcccacatg gctgcatttt tgctgctag tgattggcta    1080 gtaaggaacc aggatgagaa aggtggctgg ccaattatgg tgacccgtaa gttaggggaa    1140
gggttcaagt cttagagcc aggatggtat tctgccatgg cccaagggca agccatttct    1200
acattagtca gggcctatct gttaacaaaa gaccatatat tcctcaattc agctttaagg    1260
gcaacagccc ttataagtt tctatctgag cagcatggag ttaaagctgt gtttatgaat    1320
aaacatgact ggtatgaaga atatccaacc acacctagc cttttgtttt aaatggcttt    1380
atgtattctt taattgggct gtatgactta aagaaactg caggggaaaa actcggaaaa    1440
gaagcaaggt ccttgtatga gcgtggcatg gaatctctta aagccatgct gcccttgtat    1500
gacactggct caggaaccat ctatgacctc cgtcacttca tgcttggcat cgctcctaac    1560
ctggctcgct gggactatca taccacccac atcaatcagt tgcagctact cagtaccatt    1620
gatgagtccc caatcttcaa agaatttgtc aagaggtgga aaagctacct taaaggcagc    1680
agggcaaagc acaac                                                      1695

<210> SEQ ID NO 26
<211> LENGTH: 792
<212> TYPE: DNA
<213> ORGANISM: Mus musculus

<400> SEQUENCE: 26
ggcacagcat ccaatggttc cacacagcag ctgccacaga ccatcatcat tggggtgcgc      60
aagggtggta cccgagccct gctagagatg ctcagcctgc atcctgatgt tgctgcagct     120
gaaaacgagg tccatttctt tgactgggag gagcattaca gccaaggcct gggctggtac    180
ctcacccaga tgcccttctc ctcccctcac cagctcaccg tggagaagac acccgcctat    240
ttcacttcgc ccaaagtgcc tgagagaatc cacagcatga ccccaccat ccgcctgctg     300 cttatcctga gggacccatc agagcgcgtg ctgtccgact acacccaggt gttgtacaac    360
caccttcaga agcacaagcc ctatccaccc attgaggacc tcctaatgcg ggacggtcgg    420
ctgaacctgg actacaaggc tctcaaccgc agcctgtacc atgcacacat gctgaactgg    480
ctgcgttttt tcccgttggg ccacatccac attgtggatg gcgaccgcct catcagagac    540
cctttccctg agatccagaa ggtcgaaaga ttcctgaagc tttctccaca gatcaacgcc    600
tcgaacttct acttaacaa aaccaagggc ttctactgcc tgcgggacag tggcaaggac    660
```

| | |
|---|---|
| cgctgcttac acgagtccaa aggccgggcg cacccccagg tggatcccaa actacttgat | 720 |
| aaactgcacg aatactttca tgagccaaat aagaaatttt tcaagctcgt gggcagaaca | 780 |
| ttcgactggc ac | 792 |

<210> SEQ ID NO 27
<211> LENGTH: 1170
<212> TYPE: DNA
<213> ORGANISM: Escherichia coli

<400> SEQUENCE: 27

| | |
|---|---|
| atgcaaggta atgcactaac cgttttatta tccggtaaaa aatatctgct attgcagggg | 60 |
| ccaatgggac cctttttcag tgatgttgcc gagtggctag agtcattagg tcgtaacgct | 120 |
| gtgaatgttg tattcaacgg tggggatcgt ttttactgcc gccatcgaca atacctagct | 180 |
| tactaccaga caccgaaaga gtttcccgga tggttacggg atctccaccg gcaatatgac | 240 |
| tttgacacaa tcctctgctt tggcgactgc cgcccattgc ataaagaagc aaaacgctgg | 300 |
| gcaaagtcga aagggatccg cttcctggca tttgaagaag atatttacg cccgcaattt | 360 |
| attaccgttg aagaaggcgg agtgaacgca tattcatcgc taccgcgcga tccggatttt | 420 |
| tatcgtaagt taccagatat gcctacgccg cacgttgaga acttaaaacc ttcaacgatg | 480 |
| aaacgtatag ccatgctat gtggtattac ctgatgggct ggcattaccg tcatgagttt | 540 |
| cctcgctacc gccaccacaa atcattttcc ccctggtatg aagcacgttg ctgggttcgt | 600 |
| gcatactggc gcaagcaact ttacaaggta acacagcgta aggtattacc gaggttaatg | 660 |
| aacgaactgg accagcgtta ttatcttgct gttttgcagg tgtataacga tagccagatt | 720 |
| cgtaaccaca gcagttataa cgatgtgcgt gactatatta tgaagtcat gtactcattt | 780 |
| tcgcgtaaag cgccgaaaga aagttatttg gtgatcaaac atcatccgat ggatcgtggt | 840 |
| cacagactct atcgaccatt aattaaacgg ttgagtaagg aatatggctt aggtgagcga | 900 |
| atcctttatg tgcacgatct cccgatgccg gaattattac gccatgcaaa agcggtggtg | 960 |
| acgattaaca gtacggcggg gatctctgcg ctgattcata acaaaccact caaagtgatg | 1020 |
| ggcaatgccc tgtacgacat caagggcttg acgtatcaag gcattttgca ccagttctgg | 1080 |
| caggctgatt ttaaaccaga tatgaaactg tttaagaagt ttcgtgggta tttattggtg | 1140 |
| aagacgcagg ttaatgcggt ttattattaa | 1170 |

<210> SEQ ID NO 28
<211> LENGTH: 717
<212> TYPE: DNA
<213> ORGANISM: Escherichia coli

<400> SEQUENCE: 28

| | |
|---|---|
| atgattgttg caaatatgtc atcatacccca cctcgaaaaa aagagttggt gcattctata | 60 |
| caaagtttac atgctcaagt agataaaatt aatctttgcc tgaatgagtt tgaagaaatt | 120 |
| cctgaggaat tagatggttt ttcaaaatta atccagttaa ttccagataa agattataag | 180 |
| gatgtgggca aatttatatt tccttgcgct aaaaatgata tgatcgtact tacagatgat | 240 |
| gatattattt accctcccga ttatgtagaa aaaatgctca atttttataa ttcctttgca | 300 |
| atattcaatt gcattgttgg gattcatggc tgtatataca tagatgcatt tgatggagat | 360 |
| cagtctaaaa gaaagtatt tcatttact caagggctat tgcgaccgag agttgtaaat | 420 |
| caattaggta cagggactgt ttttcttaag gcagatcaat taccatcttt aaaatatatg | 480 |

```
gatggttctc aacgattcgt cgatgttaga ttttctcgct atatgttaga gaatgaaatt    540
ggtatgatat gtgttcccag agaaaaaaac tggctaagag aggtctcatc aggttcaatg    600
gaaggacttt ggaacacatt tacaaaaaaa tggcctttag acatcataaa agaaacacaa    660
gcaatcgcag atattcaaa acttaacctc gaattagtgt ataatgtgga agggtaa       717

<210> SEQ ID NO 29
<211> LENGTH: 1689
<212> TYPE: DNA
<213> ORGANISM: Escherichia coli

<400> SEQUENCE: 29
atgaataaat tagtgctagt cggacatcct ggctcaaagt atcagatagt tgaacatttt     60
ttgaaagaaa ttggcatgaa ctcaccaaat tattctacaa gtaataaaat ttccccagaa    120
tatatcaccg cttcattatg tcaattttat caaacaccag aagttaatga tgtagtagat    180
gagagagaat tctcagctgt tcaagtctca accatgtggg atagcatggt tcttgaacta    240
atgatgaaca atctaaataa caaactttgg gggtgggcag atccatctat aatattttt     300 cttgattttt ggaaaaatat agataaaagc ataaaattca tcatgatata tgatcaccct    360
aaatataatt taatgcgttc agtaaataat gcccctctct ctttaaatat aaataatagt    420
gtagataact ggattgcata taataaaaga ttgcttgatt ttttttttgga gaataaagaa   480 cgatgtgtgt tgattaattt tgaggcgttt caaagcaata agaaaaatat tataaagcca    540
ttgagtaata ttataaaaat agataatcta atgtctgcgc attacaaaaa ttcaatattg    600
tttgatgtgg ttgagaataa tgattataca aaatcaaatg aaattgccct gcttgaaaaa    660
tatacaactt tattttcttt aagtgcaaat gagactgaaa ttacatttaa tgatacaaag    720
gttagtgagt acttagtatc tgaattaata aagaaagaa ccgaggttct gaagctttat    780
aatgagttac aagcctatgc aaacctacct tatatagaaa catcgaaaga taacgtttcg    840
gctgaggctg cattatggga ggtagtcgaa gagagaaatt ctatcttcaa tattgtatct    900
catttggtgc aagagtcaaa aagaaggat gcagatattg aattgactaa atctatattt    960
aagaaaagac aatttttatt attgaacagg attaatgagc taaaaaaaga aaaggaagag   1020
gtaattaaac tttcaaaaat aaatcacaac gatgttgtga gacaagaaaa atatccagat   1080
gatattgaaa aaaaataaa tgacatacag aaatatgaag aagagataag cgaaaaagaa   1140
tcaaaactca ctcaggcaat atcagaaaaa gaacagattt taaacaatt gcataaatat   1200 gaagaagaga taagcgaaaa agaatcaaaa ctcactcagg caatatcaga aaagaacag   1260 attttaaaac aattgcatat agtgcaagag cagttggaac actatttat agaaaatcag   1320 gaaattaaaa agaaacttcc acctgtgcta tatggagcag ctgagcagat aaaacaagag   1380
ttaggttatc gacttggtta tattatagtc tcgtattcta aatccctcaa ggggattatt   1440
accatgccat ttgcacttat ccgtgagtgt gttttgaaa aaaacgtaa gaagagttat    1500 ggcgttgatg tgccactcta tttatatgct gatgctgata aggctgaaag agttaagaaa   1560
catttatctt atcaattagg gcaggctatt atctccagtg ctaattcgat atttggattc   1620
attacccttc catttaagtt aattgttgtt gtttataaat ataggagagc taaaatcaag   1680
ggctgttaa                                                            1689

<210> SEQ ID NO 30
<211> LENGTH: 1563
<212> TYPE: DNA
<213> ORGANISM: Escherichia coli
```

<400> SEQUENCE: 30

```
atgaacgcag aatatataaa tttagttgaa cgtaaaaaga aattagggac aaatattggt      60
gctcttgatt ttttattatc aattcataag gagaaagttg atcttcaaca taaaaactcg     120
cctttaaaag gtaacgataa ccttattcac aaaagaataa acgaatacga caatgtactt     180
gaactatcta agaatgtatc agctcagaat tctggcaatg agttttctta tttattggga     240
tatgcagatt ctcttagaaa agttggtatg ttggatactt atattaaaat tgtttgttat     300
ctaacaattc aatctcgtta ttttaaaaat ggcgaacgag ttaagctttt tgaacatata     360
agtaacgctc tacggtattc aaggagtgat tttctcatta atcttatttt tgaacgatat     420
atcgaatata taaaccatct aaaattgtcg cccaaacaaa aagatttttta tttttgtacg   480
aagttttcaa aatttcatga ttatactaaa aatggatata aatatttagc atttgataat     540
caagccgatg cagggtatgg cctgacttta ttattaaatg caaacgatga tatgcaagat     600
agttataatc tactccctga gcaagaactt tttatttgta atgctgtaat agataatatg     660
aatatttata ggagtcaatt taacaaatgt ctacgaaaat acgatttatc agaaataact     720
gatatatacc caaataaaat tatattgcaa ggaattaagt tcgataagaa aaaaaatgtt    780
tatggaaaag atcttgttag tataataatg tcagtattca attcagaaga tactattgca     840
tactcattac attcattgtt gaatcaaaca tatgaaaata ttgaaattct cgtgtgcgat     900
gattgttcat cggacaaaag ccttgaaata attaagagca tagcttattc tgattcaaga     960
gtgaaagtat atagctcacg aaaaaaccaa ggcccttata atataagaaa tgagctaata    1020
aaaaaagcac acggtaattt catcacccttt caagatgcag atgatctttc tcatccggag   1080
agaatacaaa gacaagttga ggttcttcgc aataataagg ctgtaatctg tatggctaac    1140
tggatccgtg ttgcgtcaaa tggaaaaatt caattcttct atgatgataa agccacaaga    1200
atgtctgttg tatcgtcaat gataaaaaaa gatattttttg cgacagttgg tggctataga   1260
caatctttaa ttggtgcaga tacggagttt tatgaaacag taataatgcg ttatgggcga    1320
gaaagtattg taagattact gcagccattg atattggggt tatggggaga ctccggactt    1380
accaggaata aggaacaga agctctacct gatggatata tatcacaatc tcgaagagaa    1440
tatagtgata tcgcggcaag acaacgagtg ttagggaaaa gtatcgtaag tgataaagat    1500
gtacgtggtt tattatctcg ctatggtttg tttaaagatg tatcaggaat aattgaacaa    1560
tag                                                                 1563
```

<210> SEQ ID NO 31
<211> LENGTH: 1179
<212> TYPE: DNA
<213> ORGANISM: Escherichia coli

<400> SEQUENCE: 31

```
atgttcggaa cactaaaaat aactgtttca ggcgctggtt acgttgggct ttcaaatgga     60
attctaatgg ctcaaaatca tgaagtggtt gcatttgata cccatcaaaa aaaagttgac    120
ttacttaatg ataaactctc tcctatagag gataaggaaa ttgaaaatta tctttcaact    180
aaaatactta attttcgcgc aactactaac aaatatgaag cctataaaaa tgccaattac    240
gttattattg ctacaccaac gaattatgac ccaggttcaa attactttga tacatcaagc    300
gttgaagctg tcattcgtga cgtaacggaa atcaacccaa acgcaattat ggtggttaaa    360
tctacggtcc cagtaggttt cacaaaaaca attaagaac atttaggtat taataatatt    420
```

```
atcttctctc cagaattttt acgagaagga agagccctat acgataatct ccatccatct    480
cgcattatta tcggtgaatg ttctgaacgg gcagaacgtt tggcagtgtt atttcaggaa    540
ggagcgatta aacaaaatat acccgtttta tttacagatt ctacggaagc ggaagcgatt    600
aagttatttt caaatactta tttggctatg cgagttgcat ttttttaatga attggatagt   660 tacgcagaaa gttttggtct gaatacgcgt cagattattg acggtgtttg tttggatccg    720
cgcattggta attactacaa taatccttct tttggttatg gtggctactg tttgccaaaa    780
gataccaagc aattattagc caactatcag tctgttccga ataaacttat atctgcaatt    840
gttgatgcta accgtacacg taaggacttt atcactaatg ttattttgaa acatagacca    900
caagttgtgg gggtttatcg tttgattatg aaaagtggtt cagataattt tagagattct    960
tctattcttg gtattataaa gcgtatcaag aaaaaaggcg tgaaagtaat tatttatgag   1020
ccgcttattt ctggagatac attctttaac tcacctttgg aacgggagct ggcgatcttt   1080
aaagggaaag ctgatattat tatcactaac cgaatgtcag aggagttgaa cgatgtggtc   1140
gacaaagtct atagtcgcga tttgtttaaa tgtgactaa                          1179

<210> SEQ ID NO 32
<211> LENGTH: 855
<212> TYPE: DNA
<213> ORGANISM: Escherichia coli

<400> SEQUENCE: 32
atggtactga tgatcgtcag cggacgttca ggttcaggta aatctgtcgc cctgcgtgcg     60
ctggaagata tgggttttta ctgcgtggat aaccttcccg tagtgttgtt acccgatctg    120
gctcgaactc tggccgatcg agagatttct gccgccgtca gcattgatgt tcgtaatatg    180
ccggagtcac cagaaatatt cgaacaggcg atgagtaacc tgcctgacgc tttctcaccg    240
caactactgt tcctggatgc cgaccgtaat accttaattc gtcgttacag tgacacgcgc    300
cgactgcatc cgctttccag caaaaacctg tcgctggaaa gtgctatcga caagaaagc    360 gatttgctgg agcctctgcg ttcgcgagcg gatctgattg tcgacacctc agaaatgtcc    420
gttcacgagc tggcagaaat gctgcgtacc cgtctgctgg gtaaacgtga acgtgaactg    480
accatggtct ttgagtcttt cggcttcaaa cacggtatcc ctatcgatgc agattacgtc    540
tttgacgtgc gcttcttgcc gaacccgcac tgggatccga aactgcgtcc aatgacaggt    600
cttgataaac ctgtcgccgc gttcctcgac cgccacacag aagtacacaa ttttatctac    660
cagacgcgaa gctatcttga gctatggtta cctatgctgg aaaccaacaa ccgtagctac    720
ctgacggtcg ccattggttg taccggcggg aagcaccgtt cggtgtatat tgcagagcaa    780
ctggcagact acttccgctc gcgcggtaaa aacgtccagt cacgccatcg gacgctggaa    840
aaacgtaaac catga                                                    855
```